(12) United States Patent
Love et al.

(10) Patent No.: US 9,544,313 B2
(45) Date of Patent: Jan. 10, 2017

(54) SYSTEMS, DEVICES, AND METHODS FOR AUTHENTICATION IN AN ANALYTE MONITORING ENVIRONMENT

(71) Applicant: ABBOTT DIABETES CARE INC., Alameda, CA (US)

(72) Inventors: Michael R. Love, Pleasanton, CA (US); Mark Sloan, Redwood City, CA (US); Glenn Berman, Alameda, CA (US); Nathan Crouther, San Francisco, CA (US); Gil Porat, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 14/574,017

(22) Filed: Dec. 17, 2014

(65) Prior Publication Data

US 2015/0207796 A1 Jul. 23, 2015

Related U.S. Application Data

(60) Provisional application No. 61/921,372, filed on Dec. 27, 2013.

(51) Int. Cl.
*G06F 21/00* (2013.01)
*H04L 29/06* (2006.01)
*A61B 5/1486* (2006.01)
*A61B 5/00* (2006.01)
*H04W 12/06* (2009.01)
*H04W 4/00* (2009.01)
*H04W 4/02* (2009.01)

(52) U.S. Cl.
CPC ........... *H04L 63/10* (2013.01); *A61B 5/14865* (2013.01); *A61B 5/7221* (2013.01); *H04W 4/008* (2013.01); *H04W 4/02* (2013.01); *H04W 12/06* (2013.01); *A61B 2560/0266* (2013.01)

(58) Field of Classification Search
CPC ...................................................... H04L 63/10
See application file for complete search history.

(56) References Cited

U.S. PATENT DOCUMENTS 6,377,894 B1 4/2002 Deweese et al.
6,616,819 B1 9/2003 Liamos et al.
(Continued)

FOREIGN PATENT DOCUMENTS

KR 10-2008-0051779 6/2008
KR 10-2009-0110287 10/2009
KR 10-2011-0103277 9/2011

OTHER PUBLICATIONS

WO, PCT/US2014/070945 ISR, Apr. 7, 2015.
WO, PCT/US2014/070945 IPRP, Jun. 28, 2016.

*Primary Examiner* — Morshed Mehedi
(74) *Attorney, Agent, or Firm* — One LLP

(57) ABSTRACT

Systems, devices, and methods are provided that allow the authentication of devices within analyte monitoring systems. The analyte monitoring systems can be in vivo systems and can include a sensor control device with a sensor and accompanying circuitry, as well as a reader device for communicating with the sensor control device. The analyte monitoring systems can interface with a trusted computer system located at a remote site. Numerous techniques of authentication are disclosed that can enable the detection of counterfeit components, such as a counterfeit sensor control device.

20 Claims, 15 Drawing Sheets

(56) References Cited

U.S. PATENT DOCUMENTS

| | | |
|---|---|---|
| 6,736,957 B1 | 5/2004 | Forrow et al. |
| 7,418,285 B2 | 8/2008 | Ghesquiere et al. |
| 7,501,053 B2 | 3/2009 | Karinka et al. |
| 7,749,740 B2 | 7/2010 | Eiteman et al. |
| 7,754,093 B2 | 7/2010 | Forrow et al. |
| 2002/0099942 A1* | 7/2002 | Gohl .................. G06F 21/31 713/169 |
| 2004/0118704 A1 | 6/2004 | Wang et al. |
| 2006/0091006 A1 | 5/2006 | Wang et al. |
| 2007/0118758 A1* | 5/2007 | Takahashi ............ G06F 21/305 713/186 |
| 2007/0288265 A1* | 12/2007 | Quinian .............. G06F 19/3418 705/2 |
| 2007/0288634 A1* | 12/2007 | Nakatsuyama ......... G06F 21/31 709/225 |
| 2008/0059804 A1* | 3/2008 | Shah .................. G06F 21/41 713/186 |
| 2008/0066305 A1 | 3/2008 | Wang et al. |
| 2008/0267823 A1 | 10/2008 | Wang et al. |
| 2010/0081905 A1 | 4/2010 | Bommakanti et al. |
| 2010/0094110 A1 | 4/2010 | Heller et al. |
| 2010/0094111 A1 | 4/2010 | Heller et al. |
| 2010/0094112 A1 | 4/2010 | Heller et al. |
| 2010/0230285 A1 | 9/2010 | Hoss et al. |
| 2010/0324392 A1 | 12/2010 | Yee et al. |
| 2011/0082484 A1 | 4/2011 | Saravia et al. |
| 2011/0106126 A1 | 5/2011 | Love et al. |
| 2011/0184264 A1 | 7/2011 | Galasso et al. |
| 2011/0190603 A1 | 8/2011 | Stafford |
| 2011/0191044 A1 | 8/2011 | Stafford |
| 2011/0193704 A1 | 8/2011 | Harper et al. |
| 2011/0213225 A1* | 9/2011 | Bernstein ............... G06Q 50/22 600/309 |
| 2011/0319729 A1 | 12/2011 | Donnay et al. |
| 2012/0150005 A1 | 6/2012 | Hoss et al. |
| 2012/0197222 A1 | 8/2012 | Donnay et al. |
| 2012/0260323 A1* | 10/2012 | San Vicente ........... A61B 5/002 726/6 |
| 2013/0078912 A1* | 3/2013 | San Vicente ......... A61B 5/0015 455/39 |

* cited by examiner

| Used Sensor Control Device SNs | Non-Used Sensor Control Device SNs | Region |
|---|---|---|
| Serial Number_001 | Serial Number_801 | United States |
| Serial Number_002 | Serial Number_802 | United States |
| Serial Number_003 | Serial Number_803 | United States |
| Serial Number_004 | Serial Number_910 | Germany |
| Serial Number_005 | Serial Number_911 | Germany |
| • | • | • |
| • | • | • |
| • | • | • |
| Serial Number_N | Serial Number_M | Japan |

FIG. 3C under the direction of this specification "systems, devices, and methods" can mean a single instance thereof, as well as multiples thereof.

SYSTEMS, DEVICES, AND METHODS FOR AUTHENTICATION IN AN ANALYTE MONITORING ENVIRONMENT

CROSS-REFERENCE TO RELATED APPLICATIONS

This application claims priority to U.S. Provisional Application Ser. No. 61/921,372, filed Dec. 27, 2013, which is incorporated by reference herein in its entirety for all purposes.

FIELD

The subject matter described herein relates to systems, devices, and methods for authentication in an analyte monitoring environment.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. For these and other reasons, needs exist for improved analyte monitoring systems, devices, and methods.

SUMMARY

A number of systems have been developed for the automatic monitoring of the analyte(s), like glucose, in bodily fluid such as in the blood stream, in interstitial fluid ("ISF"), dermal fluid, or in other biological fluid. Some of these systems are configured so that at least a portion of a sensor control device is positioned below a skin surface of a user, e.g., in a blood vessel or in the subcutaneous tissue of a user, so that the monitoring is accomplished in vivo. As such, these systems can be referred to as "in vivo" monitoring systems. In vivo analyte monitoring systems include "Continuous Analyte Monitoring" systems (or "Continuous Glucose Monitoring" systems) that can broadcast data from a sensor control device to a reader device continuously without prompting, e.g., automatically according to a broadcast schedule. In vivo analyte monitoring systems also include "Flash Analyte Monitoring" systems (or "Flash Glucose Monitoring" systems or simply "Flash" systems) that can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

The in vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Other devices such as personal computers have also been utilized with or incorporated into in vivo and in vitro monitoring systems.

An in vivo system manufacturer can provide users with both the sensor control device and the corresponding reader device; in some cases the two can be sold as a set. The sensor control device can have a limited lifespan and can be replaced periodically (e.g., every two weeks), but the reader device can be used for a significantly longer period of time and is reusable with each new replacement sensor control device. In those cases the manufacturer typically sells sensor control devices individually to the user.

For competitive, quality, and other reasons, manufacturers generally want users to operate only those sensor control devices made or supplied by that manufacturer, with reader devices also made or supplied by that manufacturer (or reader devices using software supplied by that manufacturer). Similarly, manufacturers may want to restrict the use of certain models of sensor control devices with certain readers, and may want to restrict the use of sensor control devices and/or readers to only certain geographic regions. Therefore, a need exists to ensure that sensor control devices supplied by a manufacturer are used only with those reader devices either supplied by that manufacturer or operating with software supplied by that manufacturer, and vice versa.

Furthermore, in recent years the threat of counterfeiting has become a greater concern. Manufacturers have a need to guard against the possibility of a third party selling "lookalike" sensor control devices that are designed for use with the manufacturer's reader device, or a device operating with software provided by the manufacturer, but are not in fact designed and built by the manufacturer.

A number of embodiments of systems, devices, and methods are provided that allow for the authentication of components within an in vivo or in vitro analyte monitoring environment. These embodiments can allow for the detection of unauthorized devices, or devices supplied by other manufacturers, as well as to restrict the types of devices, regardless of manufacturer, that are used within the environment. It should be noted that all embodiments described herein are for example only and are not intended to further limit the scope of the subject matter claimed herein beyond the explicit language of the claims themselves.

Although the analyte monitoring systems, devices, and methods can be for in vivo use, in vitro use, or both, the majority of the example embodiments will be described as operating within an in vivo analyte monitoring system.

For example, embodiments of methods of authentication in an in vivo analyte monitoring system can include receiving, by a reader device, an identifier from a sensor control device over a local wireless communication path, where the sensor control device includes a sensor and analyte monitoring circuitry, and the sensor is adapted to be inserted into a body of a user, sending the identifier from the reader device over an internet to a trusted computer system having a stored registration database, and receiving, by the reader device, an authentication result from the trusted computer system over the internet, where the authentication result indicates whether the sensor control device is or is not authorized to operate with the reader device.

In many embodiments described herein, the identifier can be a serial number of the sensor control device, a random number, one or more calibration parameters for the sensor control device, other values, and any combinations thereof.

In these and other embodiments, the methods can further include sending an identification request from the reader device over the local wireless communication path to the sensor control device, where the sensor control device sends the identifier to the reader device in response to receipt of the identification request. The methods can also include determining, by the trusted computer system, authenticity of the identifier by reference to a stored registration database. If the identifier is in the stored registration database, the methods can include determining if the identifier is associated with an unused device.

In some embodiments, the registration database can include one or more compilations of used and unused identifiers, and the methods can include updating the registration database by associating the identifier with a used device. In some embodiments, the authentication result authorizes the reader device to operate with the sensor control device if the identifier is associated with an unused device, and the authentication result does not authorize the reader device to operate (or prevents it from operating) with the sensor control device if the identifier is associated with a device that has already been used or is counterfeit.

A number of communication protocols can be used with the embodiments described herein. For example, the reader device can communicate with the sensor control device over a local wired or wireless communication link Wireless protocols that can be used include Wi-Fi, near field communication (NFC), radio frequency identification (RFID), Bluetooth, or Bluetooth Low Energy, to name a few.

A number of types of reader devices can be used with the embodiments described herein. For example, the reader device can be a smart phone, a tablet, a wearable electronic assembly such as a smart watch or smart glasses, or the like. The reader device can include location determining hardware capable of determining a current location of the reader device, such as global positioning system (GPS) hardware.

In embodiments having location determining hardware, the methods can include sending the current location of the reader device over the internet to a trusted computer system, which can generate an authentication result that either authorizes or does not authorize the reader device to operate with the sensor control device based on the current location. In some embodiments the methods can include, if the identifier is not authorized for use in the current location, displaying a message on a display of the reader device indicating that the sensor control device is not authorized for use in the current location.

The methods can further include reading, with the reader device if an authentication result permits operation of the reader device with the sensor control device and if the sensor has been inserted into the body of the user, information indicative of an analyte level of the user from the sensor control device and displaying the analyte level on a display of the reader device.

Other example embodiments are also described of in vivo analyte monitoring systems having a reader device. The reader device can include a first receiver capable of receiving an identifier and sensed analyte data from an in vivo sensor control device over the local wireless communication path, communication circuitry capable of transmitting the identifier over the internet to a trusted computer system, a second receiver capable of receiving an authentication result over the internet from the trusted computer system, and a processor programmed to read the authentication result and, if the authentication result indicates that the sensor control device is authentic, cause the sensed analyte data to be displayed to the user. If the authentication result indicates that the sensor control device is not authentic, then the processor can be programmed to cease operation of the reader device with the sensor control device. In some embodiments, the processor is further programmed to generate an identification request for transmittal by the reader device over the local wireless communication path to the sensor control device.

The system can further include the sensor control device that, in some embodiments, can include a sensor adapted to be inserted into a body of a user, analyte monitoring circuitry coupled with the sensor, a memory capable of storing an identifier, and communication circuitry capable of communicating the identifier and sensed analyte data over a local wireless communication path to the reader device.

The system can further include a trusted computer system that, in some embodiments, can include a registration database and/or a server. The trusted computer system can be programmed to verify whether the identifier received from the reader device is or is not associated with an authentic sensor control device. In some embodiments, the registration database can include a plurality of identifiers and, for each identifier within the plurality of identifiers, an indication whether the identifier is authentic. The registration database can also include one or more compilations of used and unused identifiers.

Also disclosed are example embodiments of methods of authentication within in vivo analyte monitoring systems that can include receiving, by a reader device, an identifier from a sensor control device over a local wireless communication path, where the sensor control device includes a sensor and analyte monitoring circuitry and the sensor is adapted to be inserted into the body of a user, and where the reader device includes memory having a registration database stored thereon. The methods can further include determining authenticity of the identifier by reference to the registration database, for example, by determining whether the identifier is in the stored registration database and, if so, whether the identifier is associated with an unused device.

In some embodiments, the reader device commences or continues normal operation with the sensor control device if the identifier is associated with an unused device, e.g., by receiving sensed analyte data from the sensor control device and/or displaying sensed analyte data from the sensor control device. If the identifier is associated with a device that has already been used or is counterfeit, then the reader device, in certain embodiments, does not operate with the sensor control device or terminates communications with the sensor control device.

Still other example embodiments are described of methods of authenticating in vivo analyte monitoring systems having a sensor control device and a reader device. In these other embodiments, the methods can include receiving, by a reader device, an identifier from a sensor control device over a local wireless communication path, where the sensor control device includes a sensor and analyte monitoring circuitry, and where the sensor is adapted to be inserted into a body of a user. The methods can also include receiving, by the reader device, a first token, then determining, by the reader device, if the identifier is associated with an unused sensor control device by reference to a registration database, and, if the identifier is associated with an unused sensor control device, then comparing, by the reader device, the first token with a second token stored in the registration database to determine if the first and second tokens match.

In certain embodiments, if the identifier is not associated with an unused sensor control device, then operation with the sensor control device is ceased, and the user can be notified of the same. The reader device can operate with the sensor control device if the identifier is associated with an unused device and the first and second token match.

If the first and second tokens match, then some embodiments of the methods can include reading, with the reader device, information indicative of an analyte level of the user from the sensor control device and then displaying the analyte level on a display of the reader device.

Additional example embodiments are described of methods of authenticating an in vivo analyte monitoring system having a sensor control device and a reader device. In these other embodiments, the methods can include receiving, by a reader device, an identifier from the sensor control device over a local wireless communication path, where the sensor control device includes a sensor and analyte monitoring circuitry, and where the sensor is adapted to be inserted into a body of a user. These embodiments can also include receiving a token at the reader device, where the token is known to be associated with the sensor control device, sending the identifier and the token from the reader device over an internet to a trusted computer system having a registration database, and receiving an authentication result from the trusted computer system over the internet by the reader device, where the authentication result indicates whether the sensor control device is or is not authorized to operate with the reader device.

In certain embodiments, receiving the token, at the reader device, includes receiving the token from the sensor control device over the local wireless communication path, or using an optical scanner on the reader device to scan a barcode (e.g., 2D or 3D) on a package for the sensor control device, where the barcode is representative of the token, or using a near field communication (NFC) device to scan a package for the sensor control device, where the package includes an element adapted to provide information representative of the token in response to an NFC scan. The element can be, for example, an NFC tag. In other embodiments, the token can be printed on a package for the sensor control device and the methods can include reading, by a human, the token from the package, and manually inputting the token into the reader device.

In certain embodiments, the methods can include determining, by the trusted computer system, authenticity of the identifier and the token by reference to the registration database. For example, if the identifier is present in the registration database and associated with an unused device, then it can be determined if the token received by the trusted computer system matches the token stored within the registration database. If the tokens match, then the sensor control device can be authenticated.

In some embodiments, a plurality of tokens and identifiers are stored in the registration database and only one token is associated with the identifier. If the identifier is associated with an unused device, then certain embodiments of the methods can include updating the registration database by associating the identifier with a used device.

In these and other embodiments, if the authentication result permits operation of the reader device with the sensor control device and if the sensor has been inserted into the body of the user, then the methods can include reading, with the reader device, information indicative of an analyte level of the user from the sensor control device, and displaying the analyte level on a display of the reader device.

Other example embodiments of systems, devices, and methods of authentication that use public and private keys are disclosed. For example, certain embodiments of these methods of authentication within in vivo analyte monitoring systems can include providing a private key to a reader device, where the private key is supplied by a sensor control device or a package for the sensor control device, and where the sensor control device includes a sensor and analyte monitoring circuitry and the sensor is adapted to be inserted into the body of a user, authenticating the private key using a public key stored within the reader device, and if the private key is authenticated, reading sensed analyte data from the sensor control device by the reader device.

In certain embodiments, providing the private key to the reader device includes receiving, by the reader device, the private key from the sensor control device over the local wireless communication path, scanning a barcode (e.g., 2D or 3D) on a package for the sensor control device with an optical scanner of the reader device, where the barcode is representative of the private key, or scanning a package for the sensor control device with a near field communication (NFC) device, where the package includes an element, e.g., an NFC tag, adapted to provide information representative of the private key in response to the NFC scan. In other embodiments, the private key is printed on the package for the sensor control device and the methods can include reading, by a human, the private key from the package and manually inputting the private key into the reader device.

In still other embodiments, methods of authentication within in vivo analyte monitoring systems can include digitally signing data with a private key, where the private key has a corresponding public key, storing the digitally signed data in the memory of a sensor control device, where the sensor control device includes a sensor and analyte monitoring circuitry and the sensor is configured to be inserted into the body of a user, and storing the corresponding public key in the memory of a reader device, where the reader device is capable of receiving the digitally signed data from the sensor control device and is programmed to verify that the digitally signed data is authentic using the public key.

In certain embodiments, the methods can also include determining at least one calibration parameter for the sensor, where the data that is digitally signed with the private key is the at least one calibration parameter, and where the at least one calibration parameter is determined separately for each one of a plurality of sensor control devices. Embodiments of the methods can also include storing the at least one calibration parameter, in addition to the digitally signed data, in the memory of the sensor control device. In some embodiments, the reader device is capable of receiving the at least one calibration parameter from the sensor control device and is programmed to compare the received at least one calibration parameter with the at least one calibration parameter that was digitally signed. The reader device can be programmed to operate normally with the sensor control device if the received at least one calibration parameter matches the at least one calibration parameter that was digitally signed, and can be programmed to cease operation with the sensor control device if the received at least one calibration parameter does not match the at least one calibration parameter that was digitally signed.

In all embodiments described herein that operate with a digital signature or digitally signed data, that digital signature or digitally signed data can be further encrypted prior to transfer between devices and use in a verification process.

In certain embodiments, the methods can include receiving an identifier from the reader device, the identifier having been sent to the reader device by the sensor control device, determining, by reference to the registration database, whether the identifier is or is not authentic, and sending an authentication result to the reader device, where the authentication result indicates whether the identifier is or is not authentic. The identifier can be determined to be authentic if it is not associated with a used sensor control device or a counterfeit sensor control device in the registration database. Certain embodiments of the methods can further include updating, if the identifier is determined to be authentic, the registration database to reflect that the identifier is now associated with a used sensor control device and/or downloading at least a portion of the registration database to the reader device.

In other embodiments, methods of authentication within in vivo analyte monitoring systems can include: receiving, by a reader device, digitally signed data from a sensor control device, where the sensor control device includes a sensor and analyte monitoring circuitry and the sensor is configured to be inserted into the body of a user; using, by the reader device, a public key to verify whether the digitally signed data is authentic; and determining, by the reader device, whether an identifier received from the sensor control device is or is not associated with a sensor control device that has been used, by reference to a local database stored in a memory of the reader device. In certain embodiments, the identifier is at least part of the digitally signed data and is received from the sensor control device as the digitally signed data.

For each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories, power sources, communication circuits, transmitters, receivers, processors and/or controllers that can be programmed to execute any and all method steps or facilitate the execution of any and all method steps. These sensor control device embodiments can be used and can be capable of use to implement those steps performed by a sensor control device from any and all of the methods described herein. Likewise, embodiments of reader devices are disclosed having one or more transmitters, receivers, memories, power sources, processors and/or controllers that can be programmed to execute any and all method steps or facilitate the execution of any and all method steps. These embodiments of the reader devices can be used to implement those steps performed by a reader device from any and all of the methods described herein. Embodiments of trusted computer systems are also disclosed. These trusted computer systems can include one or more processors, controllers, transmitters, receivers, memories, databases, servers, and/or networks, and can be discretely located or distributed across multiple geographic locales. These embodiments of the trusted computer systems can be used to implement those steps performed by a trusted computer system from any and all of the methods described herein.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 3B-C depict examples of data compilations, in human readable form, that could otherwise be stored, in machine-readable form, within an example embodiment of a database.

DETAILED DESCRIPTION

Figure 1:
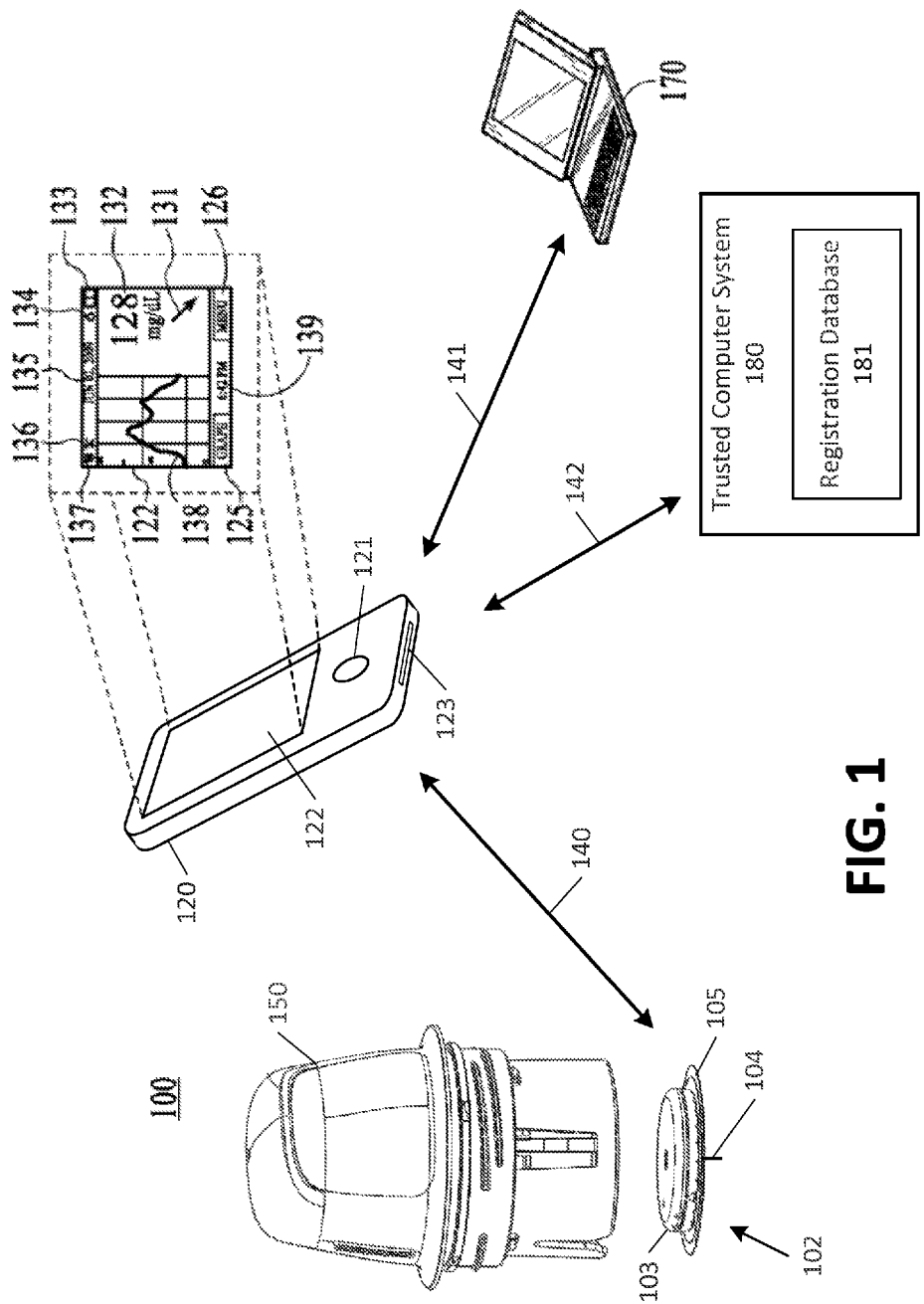
FIG. 1 is a high level diagram depicting an example embodiment of an analyte monitoring system for real time analyte (e.g., glucose) measurement, data acquisition and/or processing.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

Generally, embodiments of the present disclosure are used with in vivo systems, devices, and methods for detecting at least one analyte, such as glucose, in body fluid, (e.g., subcutaneously within the ISF or blood, or within the dermal fluid of the dermal layer). Accordingly, many embodiments include in vivo analyte sensors arranged so that at least a portion of the sensor is positioned in the body of a user to obtain information about at least one analyte of the body. It should be noted, however, that the embodiments disclosed herein can be used with in vivo analyte monitoring systems that incorporate in vitro capability, as well has purely in vitro or ex vivo analyte monitoring systems.

As mentioned, a number of embodiments of systems, devices, and methods are provided that allow for the authentication of components within an in vivo, in vitro, or ex vivo analyte monitoring environment. These embodiments can allow for the detection of unauthorized devices, or devices supplied by other manufacturers, as well as to restrict the types of devices, regardless of manufacturer, that are used within the environment. Before describing these aspects of the embodiments in detail, however, it is first desirable to describe examples of devices that can be present within, for example, an in vivo analyte monitoring system, as well as examples of their operation.

Example Embodiments of In Vivo Analyte Monitoring Systems

FIG. 1 is an illustrative view depicting an example of an in vivo analyte monitoring system 100 having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Reader device 120 is also capable of wired, wireless, or combined communication with a remote computer system 170 over communication path (or link) 141 and with trusted computer system 180 over communication path (or link) 142. Communication paths 141 and 142 can be part of a telecommunications network, such as a Wi-Fi network, a local area network (LAN), a wide area network (WAN), the internet, or other data network for uni-directional or bi-directional communication. In an alternative embodiment, communication paths 141 and 142 can be the same path. All communications over paths 140, 141, and 142 can be encrypted and sensor control device 102, reader device 120, remote computer system 170, and trusted computer system 180 can each be configured to encrypt and decrypt those communications sent and received.

Sensor control device 102 can include a housing 103 containing in vivo analyte monitoring circuitry and a power source. The in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. (Other forms of body attachment to the body may be used, in addition to or instead of adhesive.)

Sensor 104 is adapted to be at least partially inserted into the body of the user, where it can make fluid contact with that user's body fluid (e.g., interstitial fluid (ISF), dermal fluid, or blood) and be used, along with the in vivo analyte monitoring circuitry, to measure analyte-related data of the user. Sensor 104 and any accompanying sensor control electronics can be applied to the body in any desired manner. For example, also shown in FIG. 1 is an embodiment of insertion device 150 that, when operated, transcutaneously (or subcutaneously) positions a portion of analyte sensor 104 through the user's skin and into contact with the bodily fluid, and positions sensor control device 102 with adhesive patch 105 onto the skin. In other embodiments, insertion device 150 can position sensor 104 first, and then accompanying sensor control electronics can be coupled with sensor 104 afterwards, either manually or with the aid of a mechanical device. Other devices, systems, and methods that may be used with embodiments herein, including variations of sensor control device 102, are described, e.g., in U.S. Publications 2010/0324392, 2011/0106126, 2011/0190603, 2011/0191044, 2011/0082484, 2011/0319729, and 2012/0197222, the disclosures of each of which are incorporated herein by reference for all purposes.

After collecting the analyte-related data, sensor control device 102 can then wirelessly communicate that data (such as, for example, data corresponding to monitored analyte level and/or monitored temperature data, and/or stored historical analyte related data) to a reader device 120 where, in certain embodiments, it can be algorithmically processed into data representative of the analyte level of the user and then displayed to the user and/or otherwise incorporated into a diabetes monitoring regime.

As shown in FIG. 1, reader device 120 includes a display 122 to output information to the user and/or to accept an input from the user (e.g., if configured as a touch screen), and one optional input component 121 (or more), such as a button, actuator, touch sensitive switch, capacitive switch, pressure sensitive switch, jog wheel or the like, to input data or commands to reader device 120 or otherwise control the operation of reader device 120.

In certain embodiments, input component 121 of reader device 120 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals. Similar voice responsive components such as a speaker, microphone and software routines to generate, process and store voice driven signals may be provided to sensor control device 102.

In certain embodiments, display 122 and input component 121 may be integrated into a single component, for example a display that can detect the presence and location of a physical contact touch upon the display such as a touch screen user interface. In such embodiments, the user may control the operation of reader device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Reader device 120 also includes one or more data communication ports 123 for wired data communication with external devices such as a remote terminal, e.g., a personal computer. Example data communication ports include USB ports, mini USB ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Referring still to FIG. 1, display 122 can be configured to display a variety of Information—some or all of which may be displayed at the same or different time on display 122. The displayed information can be user-selectable so that a user can customize the information shown on a given display screen. Display 122 may include, but is not limited to, graphical display 138, for example, providing a graphical output of glucose values over a monitored time period (which may show: markers such as meals, exercise, sleep, heart rate, blood pressure, etc.; numerical display 132, for example, providing monitored glucose values (acquired or received in response to the request for the information); and trend or directional arrow display 131 that indicates a rate of analyte change and/or a rate of the rate of analyte change, e.g., by moving locations on display 122).

As further shown in FIG. 1, display 122 may also include: date display 135, which can provide date information for the user; time of day information display 139 providing time of day information to the user; battery level indicator display 133 graphically showing the condition of the battery (rechargeable or disposable) of reader device 120; sensor calibration status icon display 134, for example, in monitoring systems that require periodic, routine or a predetermined number of user calibration events notifying the user that the analyte sensor calibration is necessary; audio/vibratory settings icon display 136 for displaying the status of the audio/vibratory output or alarm state; and wireless connectivity status icon display 137 that provides indication of wireless communication connection with other devices such as sensor control device 102, remote computer system 170, and/or trusted computer system 180. Display 122 may further include simulated touch screen buttons 125, 126 for accessing menus, changing display graph output configurations or otherwise controlling the operation of reader device 120.

In certain embodiments, reader device 120 can be configured to output alarms, alert notifications, glucose values, etc., which may be visual, audible, tactile, or any combination thereof. Reader device 120 may include other output components such as a speaker, vibratory output component and the like to provide audible and/or vibratory output indications to the user in addition to the visual output indication provided on display 122. Further details and other display embodiments can be found in, e.g., U.S. Publication 2011/0193704, which is incorporated herein by reference for all purposes.

Reader device 120 can be connected to a remote terminal 170, such as a personal computer, which can be used by the user or a medical professional to display and/or analyze the collected analyte data. Reader device 120 can also be connected to a trusted computer system 180 that can be used for authentication of a third party software application. In both instances, reader device 120 can function as a data conduit to transfer the stored analyte level information from the sensor control device 102 to remote terminal 170 or trusted computer system 180. In certain embodiments, the received data from the sensor control device 102 may be stored (permanently or temporarily) in one or more memories of reader device 120.

Remote terminal 170 may be a personal computer, a server terminal, a laptop computer, a tablet, or other suitable data processing device. Remote terminal 170 can be (or include) software for data management and analysis and communication with the components in analyte monitoring system 100. Operation and use of remote terminal 170 is further described in the '225 Publication incorporated herein (below). Analyte monitoring system 100 can also be configured to operate with a data processing module (not shown), also as described in the incorporated '225 Publication.

Trusted computer system 180 can be within the possession of the manufacturer or distributor of sensor control device 102, either physically or virtually through a secured connection, and can be used to perform authentication of sensor control device 102. Authentication of sensor control device 102 can also be outsourced to a third-party, such that the third-party is physically in possession of trusted computer system 180. Trusted computer system 180 is trusted in the sense that system 100 can assume that it provides valid information and determinations upon which a foundation for the authentication activities can be based. Trusted computer system 180 can be trusted simply by virtue of it being within the possession or control of the manufacturer, e.g., like a typical web server. Alternatively, trusted computer system 180 can be implemented in a more secure fashion such as by requiring additional password, encryption, firewall, or other internet access security enhancements that further guard against counterfeiter attacks or attacks by computer hackers.

Trusted computer system 180 can also be referred to as registration computer system 180, or simply computer system 180. Trusted computer system 180 can include one or more computers, servers, networks, databases, and the like.

In some embodiments, trusted computer system 180 includes a registration database 181, or has secure access to a registration database, which contains comprehensive registration information for all manufactured sensor control devices 102. Upon the completion of the manufacturing process, authentication information about a particular sensor control device 102 can be stored within that sensor control device 102, placed on the packaging of that sensor control device 102, or otherwise associated with that sensor control device 102. This authentication information can also be stored within registration database 181 of trusted computer system 180 for future reference during a subsequent authentication process for that sensor control device 102.

The authentication information can be in the form of a unique identifier, where trusted computer system 180 can associate every unique identifier with a different sensor control device 102, as well as an indication whether that sensor control device 102 has not yet been used or has already been used. In these or other embodiments, authentication information can be in the form of a pair of keys, such as a private key and a public key, which are disseminated within system 100. In some embodiments, the private key is retained by trusted computer system 180 and the public key is in the possession of reader device 120 (or sensor control device 102). The keys themselves can be used for authentication, or they can be used to process digital signatures, e.g., digitally sign and un-sign data, to verify the authenticity of reader device 120 (or sensor control device 102).

The processing of data within system 100 can be performed by one or more control logic units or processors of reader device 120, remote terminal 170, trusted computer system 180, and/or sensor control device 102. For example, raw data measured by sensor 104 can be algorithmically processed into a value that represents the analyte level and that is readily suitable for display to the user, and this can occur in sensor control device 102, reader device 120, remote terminal 170, or trusted computer system 180. This and any other information derived from the raw data can be displayed in any of the manners described above (with respect to display 122) on any display residing on any of sensor control device 102, reader device 120, remote terminal 170, or trusted computer system 180.

The information may be utilized by the user to determine any necessary corrective actions to ensure the analyte level remains within an acceptable and/or clinically safe range. Other visual indicators, including colors, flashing, fading, etc., as well as audio indicators, including a change in pitch, volume, or tone of an audio output, and/or vibratory or other tactile indicators may also be incorporated into the outputting of trend data as means of notifying the user of the current level, direction, and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, an algorithm stored on a computer readable medium of system 100 can be used to determine the time it will take to reach a clinically significant level and can be used to output a notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring now in further detail to reader device 120, that device 120 can be a mobile communication device such as a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 2A:
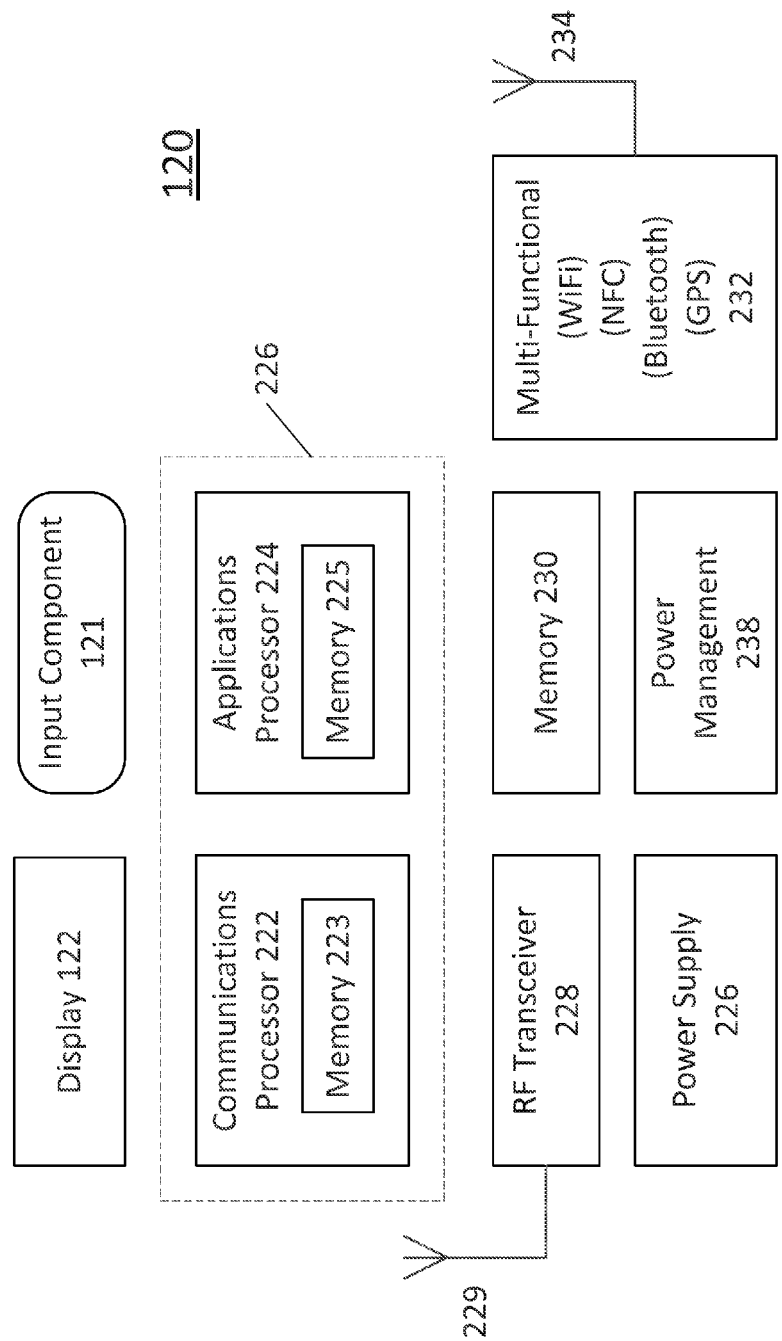
FIG. 2A is a block diagram depicting an example embodiment of a reader device.

FIG. 2A is a block diagram of an example embodiment of a reader device 120 configured as a smart phone. Here, reader device 120 includes an input component 121, display 122, and processing hardware 226, which can include one or more processors, microprocessors, controllers, and/or microcontrollers, each of which can be a discrete chip or distributed amongst (and a portion of) a number of different chips. Here, processing hardware 226 includes a communications processor 222 having on-board memory 223 and an applications processor 224 having on-board memory 225. Reader device 120 further includes an RF transceiver 228 coupled with an RF antenna 229, a memory 230, multi-functional circuitry 232 with one or more associated antennas 234, a power supply 236, and power management circuitry 238. FIG. 2A is an abbreviated representation of the typical hardware and functionality that resides within a smart phone and those of ordinary skill in the art will readily recognize that other hardware and functionality (e.g., codecs, drivers, glue logic, can also be included here.

Communications processor 222 can interface with RF transceiver 228 and perform analog-to-digital conversions, encoding and decoding, digital signal processing and other functions that facilitate the conversion of voice, video, and data signals into a format (e.g., in-phase and quadrature) suitable for provision to RF transceiver 228, which can then transmit the signals wirelessly. Communications processor 222 can also interface with RF transceiver 228 to perform the reverse functions necessary to receive a wireless transmission and convert it into digital data, voice, and video.

Applications processor 224 can be adapted to execute the operating system and any software applications that reside on reader device 120, process video and graphics, and perform those other functions not related to the processing of communications transmitted and received over RF antenna 229. The smart phone operating system will operate in conjunction with a number of applications on reader device 120. Any number of applications can be running on reader device 120 at any one time, and will typically include one or more applications that are related to a diabetes monitoring regime, in addition to the other commonly used applications that are unrelated to such a regime, e.g., email, calendar, weather, sports, games, etc.

Memory 230 can be shared by one or more the various functional units present within reader device 120, or can be distributed amongst two or more of them (e.g., as separate memories present within different chips). Memory 230 can also be a separate chip of its own. Memory 230 is nontransitory, and can be volatile (e.g., RAM, etc.) and/or non-volatile memory (e.g., ROM, flash memory, F-RAM, etc.).

Multi-functional circuitry 232 can be implemented as one or more chips and/or components (e.g., transmitter, receiver, transceiver, and/or other communication circuitry) that perform other functions such as local wireless communications (e.g., for Wi-Fi, Bluetooth, Bluetooth Low Energy, Near Field Communication (NFC), Radio Frequency Identification (RFID), and others) and determining the geographic position of reader device 120 (e.g., global positioning system (GPS) hardware). One or more other antennas 234 are associated with the functional circuitry 232 as needed to operate with the various protocols and circuits.

Power supply 236 can include one or more batteries, which can be rechargeable or single-use disposable batteries. Power management circuitry 238 can regulate battery charging and power supply monitoring, boost power, perform DC conversions, and the like.

As mentioned, the reader device 120 may also include one or more data communication ports such as USB port (or connector) or RS-232 port (or any other wired communication ports) for data communication with a remote terminal 170, trusted computer system 180, or sensor control device 102, to name a few.

Reader device 120 may include a strip port (not shown) or be coupled with a strip port module (not shown) configured to receive in vitro test strips. In such a configuration, reader device 120 can process a fluid sample on a test strip, determine an analyte level contained therein, and display that result to a user. Any suitable in vitro test strip may be employed, e.g., test strips that only require a very small amount (e.g., one microliter or less, e.g., about 0.5 microliter or less, e.g., about 0.1 microliter or less), of applied sample to the strip in order to obtain accurate glucose information, e.g. FreeStyle® or Precision® blood glucose test strips and systems from Abbott Diabetes Care Inc. Reader devices with in vitro monitors and test strip ports may be configured to conduct in vitro analyte monitoring with no user calibration in vitro test strips (i.e., no human intervention calibration), such as FreeStyle Lite glucose test strips from Abbott Diabetes Care Inc. Detailed description of such test strips and devices for conducting in vitro analyte monitoring is provided in U.S. Pat. Nos. 6,377,894, 6,616,819, 7,749,740, 7,418,285; U.S. Published Patent Publication Nos. 2004/0118704, 2006/0091006, 2008/0066305, 2008/0267823, 2010/0094110, 2010/0094111, and 2010/0094112, and 2011/0184264, the disclosure of each of which are incorporated herein by reference for all purposes. The present inventive subject matter can be used with and/or in the systems, devices, and methods described in these incorporated references.

Figure 2B:
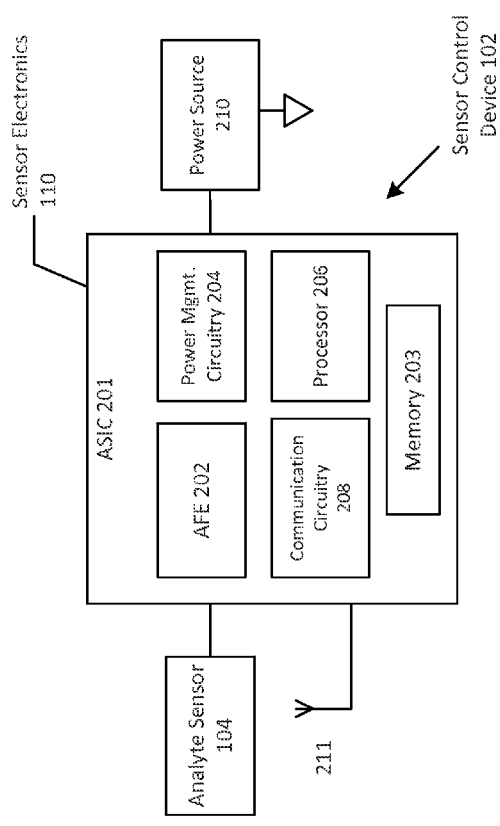
FIGS. 2B-C are block diagrams depicting example embodiments of a sensor control device.
Figure 2C:
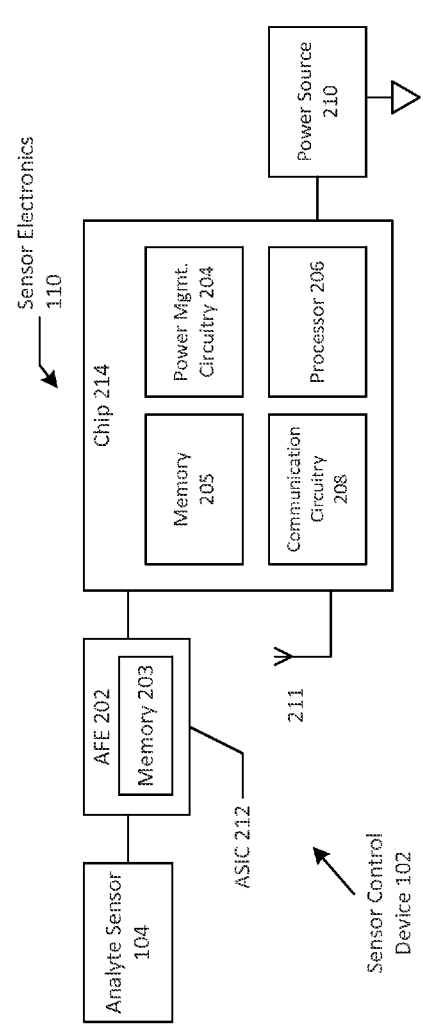

FIGS. 2B-C are block schematic diagrams depicting example embodiments of sensor control device 102 having analyte sensor 104 and sensor electronics 110 (including analyte monitoring circuitry) that can have the majority of the processing capability for rendering end-result data suitable for display to the user. In FIG. 2B, a single semiconductor chip 201 is depicted that can be a custom application specific integrated circuit (ASIC). Shown within ASIC 201 are certain high-level functional units, including an analog front end (AFE) 202, power management (or control) circuitry 204, processor 206, and communication circuitry 208 (which can be implemented as a transmitter, receiver, transceiver, passive circuit, or otherwise according to the communication protocol). In this embodiment, both AFE 202 and processor 206 are used as analyte monitoring circuitry, but in other embodiments either circuit can perform the analyte monitoring function. Processor 206 can include one or more processors, microprocessors, controllers, and/or microcontrollers, each of which can be a discrete chip or distributed amongst (and a portion of) a number of different chips.

A memory 203 is also included within ASIC 201 and can be shared by the various functional units present within ASIC 201, or can be distributed amongst two or more of them. Memory 203 can also be a separate chip. Memory 203 can be volatile and/or non-volatile memory. In this embodiment, ASIC 201 is coupled with power source 210, which can be a coin cell battery, or the like. AFE 202 interfaces with in vivo analyte sensor 104 and receives measurement data therefrom and outputs the data to processor 206 in digital form, which in turn processes the data to arrive at the end-result glucose discrete and trend values, etc. This data can then be provided to communication circuitry 208 for sending, by way of antenna 211, to reader device 120 (not shown) where minimal further processing is needed by the resident software application to display the data.

FIG. 2C is similar to FIG. 2B but instead includes two discrete semiconductor chips 212 and 214, which can be packaged together or separately. Here, AFE 202 is resident on ASIC 212. Processor 206 is integrated with power management circuitry 204 and communication circuitry 208 on chip 214. AFE 202 includes memory 203 and chip 214 includes memory 205, which can be isolated or distributed within. In one example embodiment, AFE 202 is combined with power management circuitry 204 and processor 206 on one chip, while communication circuitry 208 is on a separate chip. In another example embodiment, both AFE 202 and communication circuitry 208 are on one chip, and processor 206 and power management circuitry 204 are on another chip. It should be noted that other chip combinations are possible, including three or more chips, each bearing responsibility for the separate functions described, or sharing one or more functions for fail-safe redundancy.

Performance of the data processing functions within the electronics of the sensor control device 102 provides the flexibility for system 100 to schedule communication from sensor control device 102 to reader device 120, which in turn limits the number of unnecessary communications and can provide further power savings at sensor control device 102.

Information may be communicated from sensor control device 102 to reader device 120 automatically and/or continuously when the analyte information is available, or may not be communicated automatically and/or continuously, but rather stored or logged in a memory of sensor control device 102, e.g., for later output. Accordingly, in many embodiments of system 100, analyte information derived by sensor control device 102 is made available in a user-usable or viewable form only when queried by the user such that the timing of data communication is selected by the user.

Data can be sent from sensor control device 102 to reader device 120 at the initiative of either sensor control device 102 or reader device 120. For example, in some example embodiments sensor control device 102 can communicate data periodically in a broadcast-type fashion, such that an eligible reader device 120, if in range and in a listening state, can receive the communicated data (e.g., sensed analyte data). This is at the initiative of sensor control device 102 because reader device 120 does not have to send a request or other transmission that first prompts sensor control device 102 to communicate. Broadcasts can be performed, for example, using an active Wi-Fi, Bluetooth, or BTLE connection. The broadcasts can occur according to a schedule that is programmed within device 102 (e.g., about every 1 minute, about every 5 minutes, about every 10 minutes, or the like). Broadcasts can also occur in a random or pseudorandom fashion, such as whenever sensor control device 102 detects a change in the sensed analyte data. Further, broadcasts can occur in a repeated fashion regardless of whether each broadcast is actually received by a reader device 120.

System 100 can also be configured such that reader device 120 sends a transmission that prompts sensor control device 102 to communicate its data to reader device 120. This is generally referred to as "on-demand" data transfer. An on-demand data transfer can be initiated based on a schedule stored in the memory of reader device 120, or at the behest of the user via a user interface of reader device 120. For example, if the user wants to check his or her analyte level, the user could perform a scan of sensor control device 102 using an NFC, Bluetooth, BTLE, or Wi-Fi connection. Data exchange can be accomplished using broadcasts only, on-demand transfers only, or any combination thereof.

Accordingly, once a sensor control device 102 is placed on the body so that at least a portion of sensor 104 is in contact with the bodily fluid and electrically coupled to the electronics within device 102, sensor derived analyte information may be communicated in on-demand or broadcast fashion from the sensor control device 102 to a reader device 120. On-demand transfer can occur by first powering on reader device 120 (or it may be continually powered) and executing a software algorithm stored in and accessed from a memory of reader device 120 to generate one or more requests, commands, control signals, or data packets to send to sensor control device 102. The software algorithm executed under, for example, the control of processing hardware 226 of reader device 120 may include routines to detect the position of the sensor control device 102 relative to reader device 120 to initiate the transmission of the generated request command, control signal and/or data packet.

Different types and/or forms and/or amounts of information may be sent as part of each on-demand or broadcast transmission including, but not limited to, one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), or historical analyte information corresponding to analyte information obtained prior to a given reading and stored in a memory of sensor control device 102.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, reader device 120 will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be communicated from sensor control device 102 with each data communication. The temperature reading or measurement, however, may be used in conjunction with a software routine executed by reader device 120 to correct or compensate the analyte measurement output to the user by reader device 120, instead of or in addition to actually displaying the temperature measurement to the user.

US Patent Application Publ. No. 2011/0213225 (the '225 Publication) generally describes components of an in vivo-based analyte monitoring system that are suitable for use with the authentication methods and hardware embodiments described herein. The '225 Publication is incorporated by reference herein in its entirety for all purposes. For other examples of sensor control device 102 and reader device 120, see, e.g., devices 102 and 120, respectively, as described in the incorporated '225 Publication.

Example Embodiments of Authentication Systems, Devices, and Methods

In many conventional in vivo systems, the sensor control device and reader device communicate with each other over a proprietary wireless protocol that cannot easily be deciphered by third parties. The presence of this proprietary wireless protocol acts as a barrier to the usage of unauthorized sensor control or reader devices within the in vivo system.

However, with the integration of in vivo monitoring software into commercially available communication devices like smart phones and the use of those smart phones to communicate with the sensor control device using well known communication protocols (e.g., Wi-Fi, NFC, RFID, Bluetooth, BTLE, etc.), the proprietary communication link can no longer act as a de facto technique for authentication. Accordingly, other techniques and hardware for authentication are required.

A number of example embodiments of enhanced systems, devices, and methods for providing authentication are described herein. In these embodiments, the device being authenticated will most commonly be sensor control device 102. It should be understood, however, that the techniques and features described herein can also be used to authenticate other devices and components of system 100 other than sensor control device 102. For instance, in certain embodiments, reader device 120 can be authenticated using similar techniques and features to those described herein.

Generally, to operate in vivo monitoring system 100, a user will first remove, or cause to be removed, sensor control device 102 from sterile packaging. Sensor control device 102 can then be placed on the user's body such that sensor 104 is in contact with the user's body fluid. As mentioned, this can be done with the aid of an inserter 150. In many embodiments, sensor control device 102 will be activated as will reader device 120. A connection will also be established between sensor control device 102 and reader device 120 so that they may exchange data and information. These events can occur in a number of different sequences. For instance, activation of sensor control device 102 can occur prior to removal from packaging, upon the removal from packaging, or subsequent to the removal from packaging (either before or after placement on the user's body). Activation of reader device 120 can also occur at any of those times. Reader device 120, in some embodiments can be a smart phone, in which case it will likely have been activated long before activation of sensor control device 102. In fact, reader device 120 may have interfaced with any number of sensor control devices 102 prior to the current one. By way of further example, the connection between sensor control device 102 and reader device 120 can be established prior to the removal of sensor control device 102 from its packaging, upon the removal of sensor control device 102 from its packaging, or subsequent to the removal of sensor control device 102 from its packaging (either before or after placement of sensor control device 102 on the user's body).

Authentication of sensor control device 102 can also occur at any time during the usage of that sensor control device 102. For instance, authentication can occur prior to the removal of sensor control device 102 from its packaging, upon removal of sensor control device 102 from its packaging, or subsequent to removal of sensor control device 102 from its packaging (either before or after placement of sensor control device 102 on the user's body). Authentication can occur during the establishment of a connection between sensor control device 102 and reader device 120, for example, during or immediately after the pairing of sensor control device 102 with reader device 120 if a pairing procedure is used, such as with a Bluetooth protocol. Authentication can occur after establishing a connection between sensor control device 102 and reader device 120 but prior to the monitoring of analyte levels by sensor control device 102, or prior to the reception of those monitored analyte levels by reader device 120.

In still other embodiments, authentication can occur after sensor control device 102 has monitored the analyte levels, transferred those analyte levels to reader device 120, and reader device 120 has displayed those analyte levels to the user or otherwise communicated them to the user or to another computer system for display and/or analysis. In most embodiments, the purpose of authentication of sensor control device 102 is to detect the presence of counterfeit sensor control devices and prevent their usage in system 100, meaning that authentication provides the greatest benefits when it occurs prior to actual use of sensor control device 102 to measure and/or communicate measured analyte levels of the user. Thus, while delay in the authentication process is permissible, it may not be the most desirable (depending on the implementation).

The authentication process can be initiated by either sensor control device 102 or reader device 120. For instance, reader device 120 can send an identification request or command to sensor control device 102 so that sensor control device 102 can initiate the authentication process, for instance, by sending authentication information to reader device 120. The identification request or command need not be dedicated for the purpose of initiating the authentication process. Rather, the request or command can instead be data, e.g., header or payload data, that is used primarily for other purposes but is interpreted, e.g., upon initial receipt, as a trigger for the sending of authentication information by sensor control device 102.

Alternatively, sensor control device 102 can initiate the authentication process by automatically supplying authentication information to reader device 120 without having received a prior request to do so. Sensor control device 102 may broadcast authentication information upon activation, or upon establishing a connection with reader device 120, upon receiving a first communication from reader device 120, or the like. Sensor control device 102 can also be configured to continuously send authentication information until the receipt of an acknowledgment from reader device 120. Sensor control device 102 may include authentication information within all (or most) communications as a matter of course, to allow reader device 120 to read the authentication information when desired, and also to allow multiple reader devices 120 to operate with sensor control device 102 without having to send multiple authentication information requests.

Figure 3A:
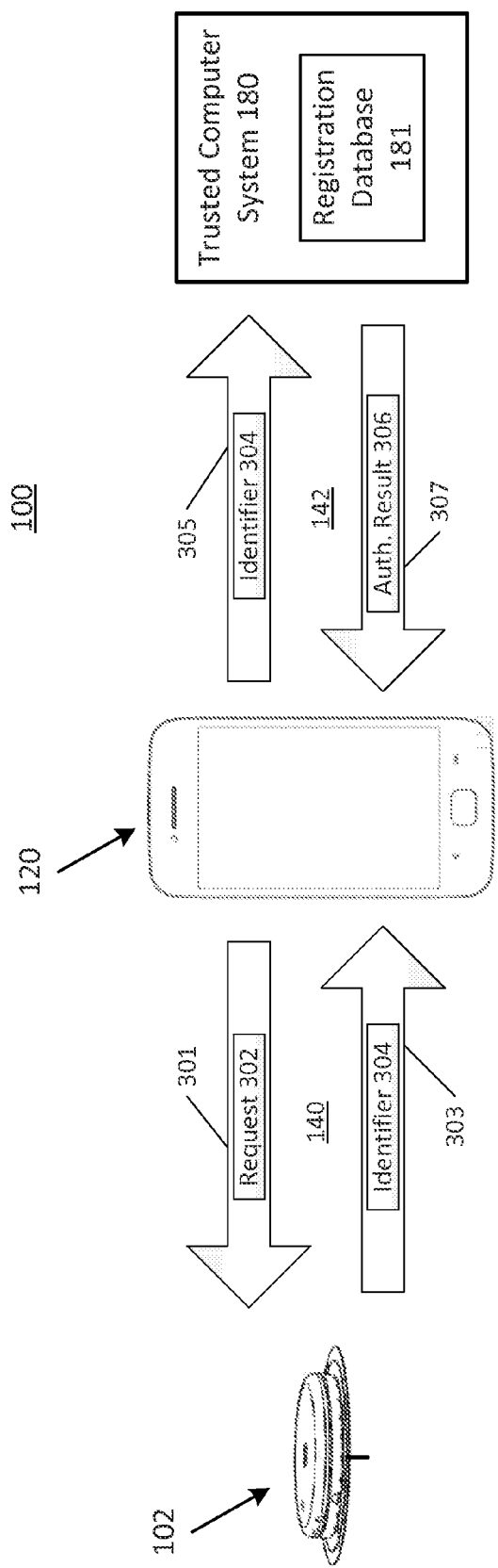
FIG. 3A is an illustration depicting an example embodiment of an in vivo monitoring system having authentication capability.

FIG. 3A is an illustration depicting an example embodiment of in vivo analyte monitoring system 100. Here, sensor control device 102 is in communication with reader device 120 over a local wireless communication path 140. Reader device 120 is in communication with trusted computer system 180 over communication path 142, which in this embodiment is the internet. Sensor control device 102 includes a memory (e.g., memory 203 and/or 205 as shown in FIGS. 2B-C) that stores authentication information about sensor control device 102. This authentication information can, in certain embodiments, uniquely identify sensor control device 102 such that no two sensor control devices 102 (within the same product line) share the same authentication information. In many embodiments, the authentication information is an identification (ID) number of sensor control device 102 or sensor 104 (also referred to herein as an "identifier"), e.g., a serial number, that is assigned to sensor control device 102 and stored within memory 203 and/or 205 during the manufacturing or post manufacturing process. Identifiers 304 can be chosen as a non-sequential, random, or pseudo-random string of characters (alphanumeric or otherwise) to minimize the risk that a counterfeiter will be able to forecast or correctly guess future identifiers 304.

FIG. 3A depicts system 100 with the sending of communications at different points in time. For example, reader device 120 first transmits communication 301 (or transmission, message, packet, etc.), containing an authentication request 302, to sensor control device 102 over communication path 140. After receiving and reading authentication request 302, sensor control device 102 can send a communication 303, containing identifier 304, back to reader device 120 over path 140. Reader device 120, after receiving identifier 304, can optionally perform a first verification to ensure that identifier 304 is in the proper format or that identifier 304 does not belong to a class of devices (e.g., prior models) that are not for operation with reader device 120.

Reader device 120 can then transmit a communication 305, containing identifier 304 (in the same or a different format from that received), over communication path 142 to trusted computer system 180. Trusted computer system 180 includes computer hardware that is programmed to read the received identifier 304 and compare it to a compilation of identifiers stored therewith, such as within registration database 181. The compilation can be in any desired form, including but not limited to a data structure, table, list, array, and the like. The compilation can also be contiguous or non-contiguous, e.g., spread across multiple data structures. In certain embodiments, each identifier stored within registration database 181 is associated with an indication as to whether that identifier correlates to a sensor control device 102 that has already been used.

Figure 3B:
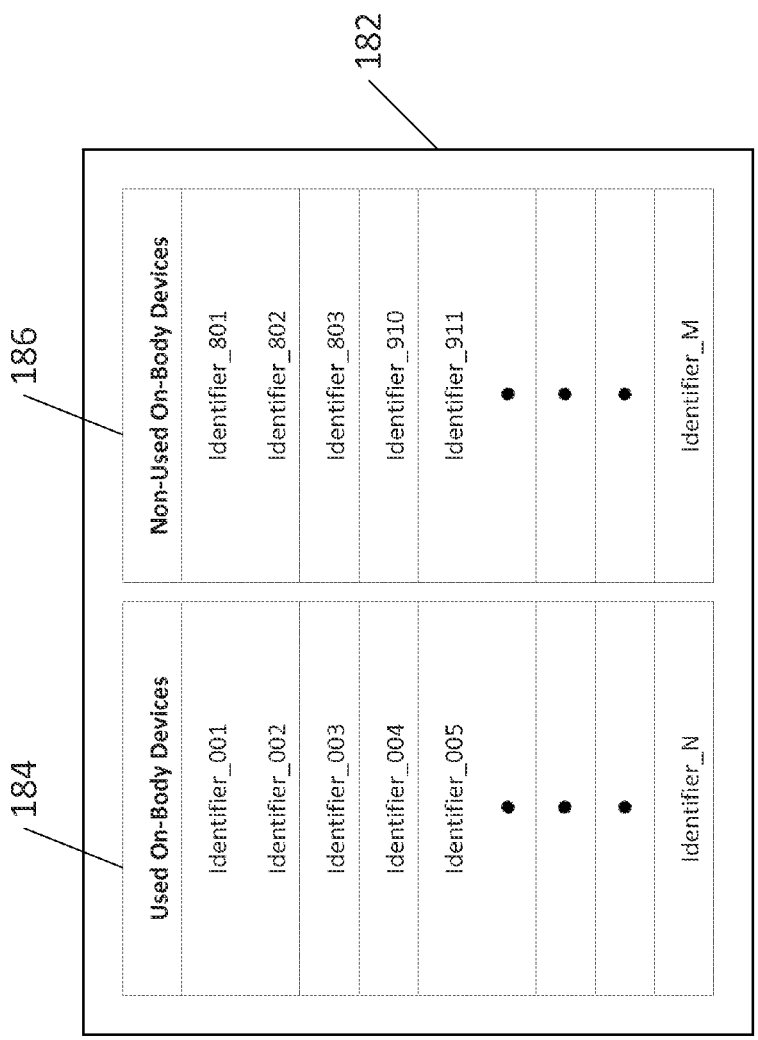

FIG. 3B depicts an example of a compilation 182 of identifiers 304 in a table format. In most embodiments, compilation 304 would be stored in a computer readable format different from the human readable format shown here. Each identifier 304 is contained within one of two separate lists: a first list 184 of identifiers 304 that are associated with sensor control devices 102 that have already been used; or a second list 186 of identifiers 304 that are associated with sensor control devices 102 that have not yet been used. Trusted computer system 180 can consult the compilation of unused sensor control devices 102 first and the compilation of used sensor control devices 102 second or vice-versa.

Alternatively, compilation 182 can include only unused identifiers 304, where a failure to locate the received identifier 304 within that compilation corresponds to a conclusion that the received identifier 304 is associated with an already used sensor control device 102, a sensor control device 102 that is not authorized for use with reader device 120, or a sensor control device 102 that is counterfeit. Once a particular identifier 304 is located within the compilation it would then be removed. Of course, a reverse scheme can also be implemented where compilation 182 only includes used identifiers 304.

Should a received identifier 304 be located on list 186, then trusted computer system 180 associates that received identifier 304 with a sensor control device 102 that is authentic (e.g., not made by a different manufacturer), or authorized for use by the user with reader device 120. Trusted computer system 180 then generates an authentication result 306 that authorizes the use of sensor control device 102 and transmits that authentication result 306 in communication 307 over communication path 142 to reader device 120. Authentication result 306 can be one or more bits of data (e.g., a flag or notification) that indicate whether or not sensor control device 102 is permitted for use, and also optionally any other related information, such as the reason(s) for a failure to authenticate. Authentication result 306 can be interpreted by reader device 120 as a command to continue or to stop operation with sensor control device 102.

Trusted computer system 180 also revises compilation 182 such that the received identifier 304 is then associated with a used sensor control device 102. In this embodiment, this would entail moving that identifier 304 from list 186 to list 184. Reader device 120 receives and reads the authentication result 306, thereby becoming informed that sensor control device 102 is an authentic device.

Reader device 120 can then optionally display the positive authentication result to the user. Reader device 120 can be programmed to then initiate (or, alternatively, to then continue) normal operation with sensor control device 102, such as by receiving monitored analyte data from sensor control device 102 and displaying that information, e.g., in the form of a glucose level, to the user.

Alternatively, should a received identifier 304 be located on list 184, then trusted computer system 180 associates that received identifier with a sensor control device 102 that is not authentic, or not authorized for use by the user with reader device 120. In such an instance, it is possible that sensor control device 102 is an unused counterfeit device, that sensor control device 102 had already been used once and an attempt is being made to reuse that same sensor control device 102, or that sensor control device 102 is a refurbished or recycled device. Other possibilities may also exist. Trusted computer system 180 then generates an authentication result 306 that indicates that the use of sensor control device 102 is not permitted or authorized, and transmits that negative authentication result 306 over communication path 142 to reader device 120. Reader device 120 receives and reads the authentication result 306, thereby becoming informed that sensor control device 102 is not authorized. Reader device 120 can be programmed to then cease operation with sensor control device 102, or otherwise prevent the use of that particular sensor control device 102. Reader device 120 can optionally display the negative authentication result to the user and instruct the user to remove sensor control device 102 if it has already been applied to the user's body. Reader device 120 can optionally inform the user that the sensor control device is a counterfeit device.

In some embodiments, reader device 120 includes local positioning capability that determines its geographic position. Because the reader device 120 is typically used in close proximity with sensor control device 102, e.g., by the same user, it can be assumed that sensor control device 102 will have the same geographic location has reader device 120. Referring back to FIG. 3A, reader device 120 can transmit current location information along with identifier 304 in communication 305. The current location information can be used by trusted computer system 180 to assess whether sensor control device 102 is being used within an authorized geographic region. Authorized geographic regions can be segmented on the basis of continents, nations, or other regions as desired. Such an assessment can help ensure that sensor control device 102 is used only in regions where the device has regulatory or other requisite governmental approval.

FIG. 3C depicts an example embodiment of compilation 182 having regional information further included therein. In this embodiment, list 186 includes those identifiers 304 that are associated with unused sensor control devices 102 within a first partition 187 and those regions in which the corresponding sensor control device 102 is approved for use within a second partition 188. Thus, if identifier 304 is located by system 180 within partition 187 of list 186, then system 180 can further compare the received location information with the approved regions in partition 188. If it is determined that the current location of the unused sensor control device 102 is within an approved region, then trusted computer system 180 can generate a positive authentication result 306 (an approval indication) and transmit that positive authentication result 306 to reader device 120. Reader device 120 can then treat sensor control device 102 as an authorized device. Should it be determined that the current location of the unused sensor control device 102 is not within an approved region, then trusted computer system 180 can generate a negative authentication result 306 (withheld authorization) and transmit that result 306 to reader device 120.

Alternatively, system 180 can generate a hybrid authentication result 306 that indicates that sensor control device 102 is authentic but not in the proper region. Reader device 120 can be programmed to allow temporary use of sensor control device 102 in the improper region, for example, if the user is traveling. Reader device 120 can cease operation with sensor control device 102 and, optionally display or otherwise communicate that result to the user.

In other embodiments, reader device 120 can locally store information that correlates particular sensor control devices 102 with the regions in which they are approved for use. In those cases, reader device 120 can locally determine whether a particular sensor control device 102 is approved for use in a particular region without having to communicate first with another computer system over the internet to obtain that authorization.

Figure 3D:
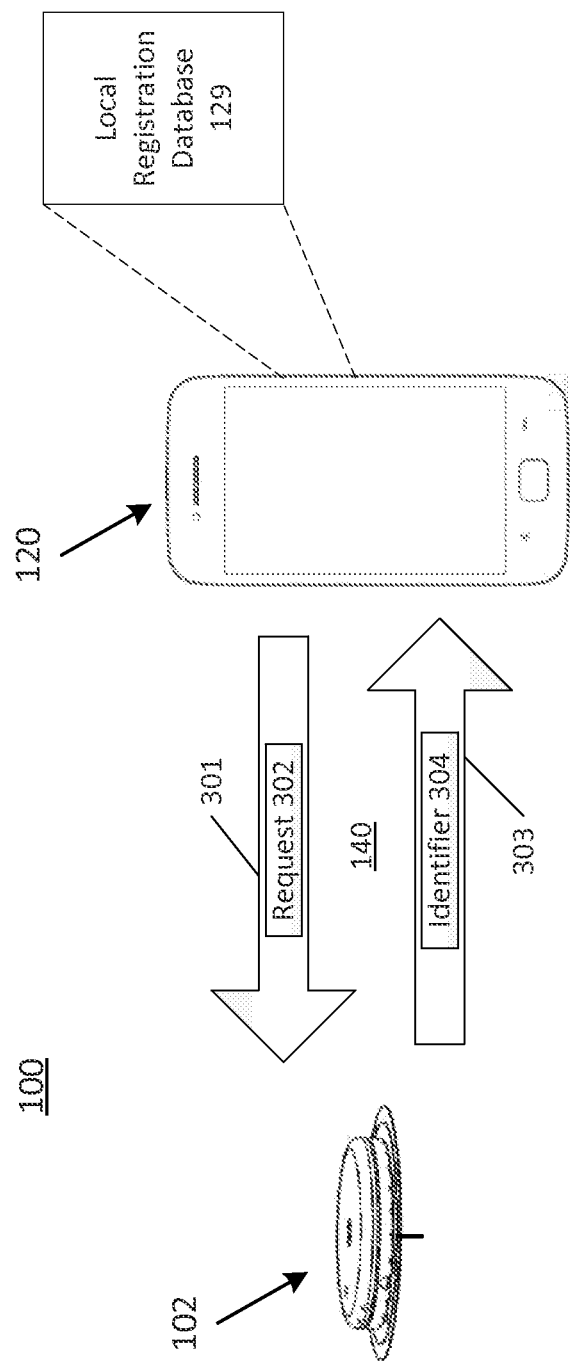
FIG. 3D is an illustration depicting another example embodiment of an in vivo monitoring system having authentication capability.

FIG. 3D is an illustration depicting another example embodiment of system 100. This embodiment is similar to that described with respect to FIG. 3A except that reader device 120 locally stores a registration database 129 (similar to registration database 181) and can use registration database 129 to perform an authentication of sensor control device 102 without the need for an internet connection to a remote network having trusted computer system 180. Thus, reader device 120 need not always have internet access to perform authentication, thereby allowing the user added flexibility in using system 100. Database 129 is stored within the local memory (e.g., memory 263 as depicted in FIG. 2B) of reader device 120, for example, during manufacturing, and can be accessed at any time. Similar to the embodiments described above, reader device 120 can, optionally, first send an authentication request 302 to sensor control device 102 in communication 301. Sensor control device 102 can then respond with identifier 304 in communication 303. After receiving identifier 304, reader device 120 can consult database 129 to determine if identifier 304 is associated with a used or unused device in a manner similar to that described with respect to FIGS. 3A-C.

Local registration database 129 can be updated once an internet connection is established by reader device 120. In another embodiment, new sensor control devices 102 (e.g., individually or in a multi-pack) can be provided to users with updates to local registration database 129 stored therein, where those updates are subsequently communicated wirelessly or otherwise uploaded to reader device 120. In yet another embodiment, the updates to database 129 can be provided with new sensor control devices 102 by way of barcodes or NFC (or RFID) elements that contain the updates and can provide the update to reader device 120 through a corresponding optical, NFC, or RFID scan.

In an update, identifiers 304 associated with newly manufactured sensor control devices 102 can be appended to database 129, and those sensor control devices 102 that were marked as unused within database 129, which have recently been used by a user, can be updated accordingly within database 129. In addition, when an internet connection is established, reader device 120 can report the fact that identifier 304 of the current sensor control device 102 has now been used to trusted computer system 180 so that it may update database 181 and report the same to other reader devices 120 in the field.

In certain embodiments, database 181 acts as a master database that can be used to resolve any conflicts between databases 129 of reader devices 120 in the field. Trusted computer system 180 can also send a message or command to a particular reader device 120 that has been used with a counterfeit or unauthorized sensor control device 102 that instructs that reader device 120 to establish an internet connection prior to commencing normal operation (e.g., reading and reporting sensed analyte data) with any future sensor control devices 102. This can effectively designate those reader devices 120 that have been used with counterfeit sensor control devices 102 as higher risk devices that may be more likely to be used with counterfeit sensor control devices 102 in the future. The more stringent safeguard is the requirement that those reader devices 120 establish an interconnect connection and perform an authentication procedure with trusted computer system 180 prior to commencing normal operation with any particular sensor control device 102.

Figure 4:
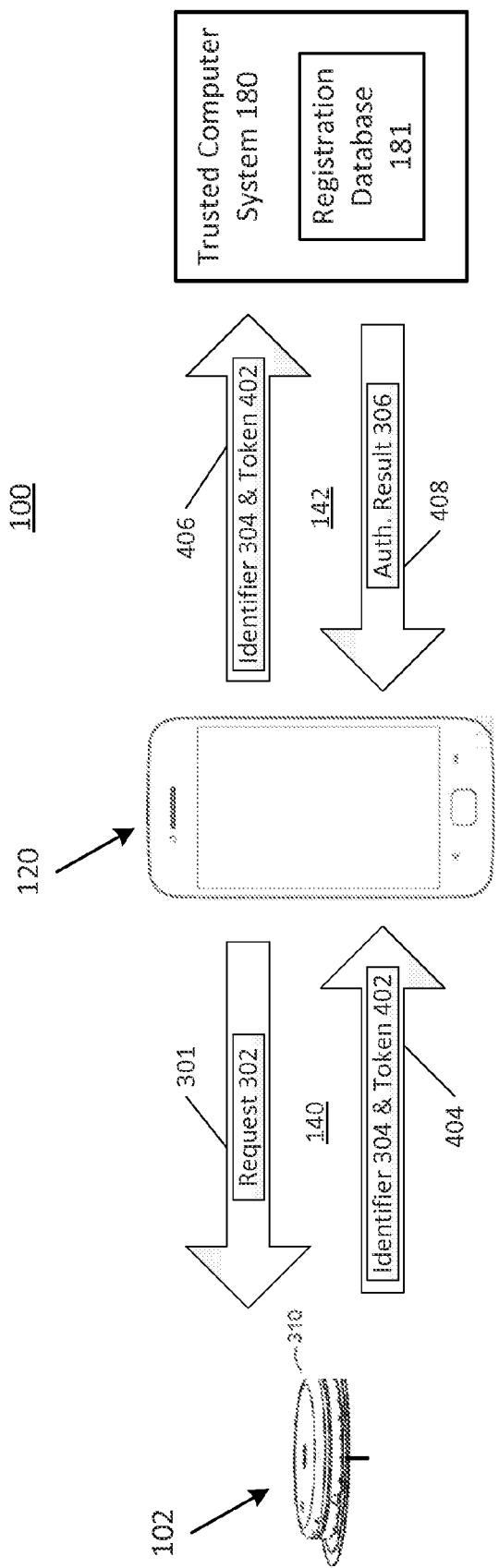
FIGS. 4-7 are illustrations depicting additional example embodiments of in vivo monitoring systems having various authentication capabilities.
Figure 5A:
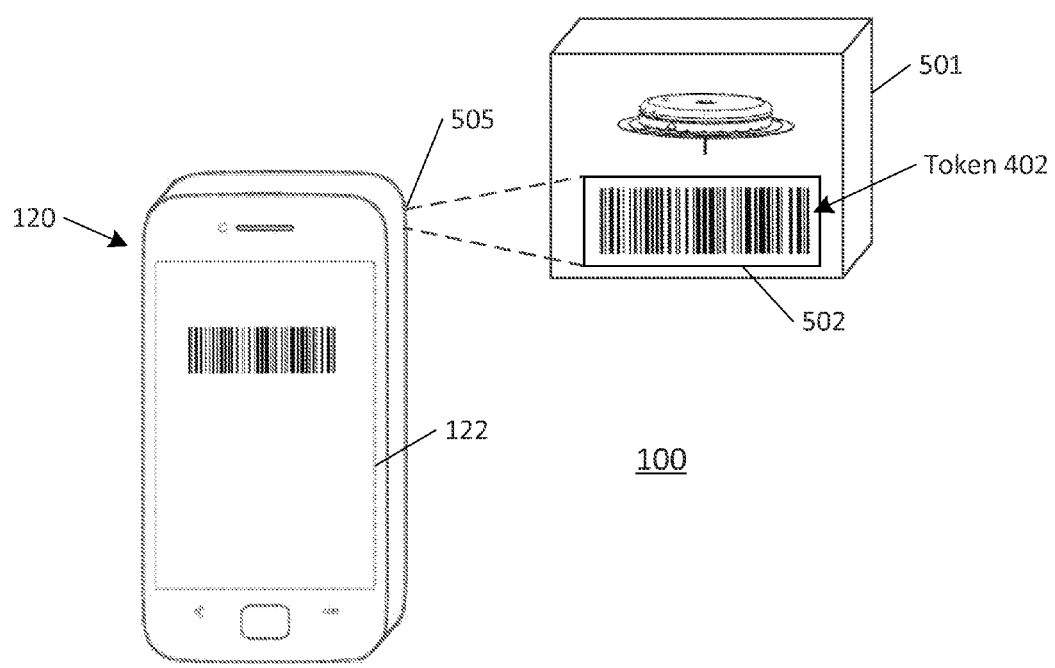
Figure 5B:
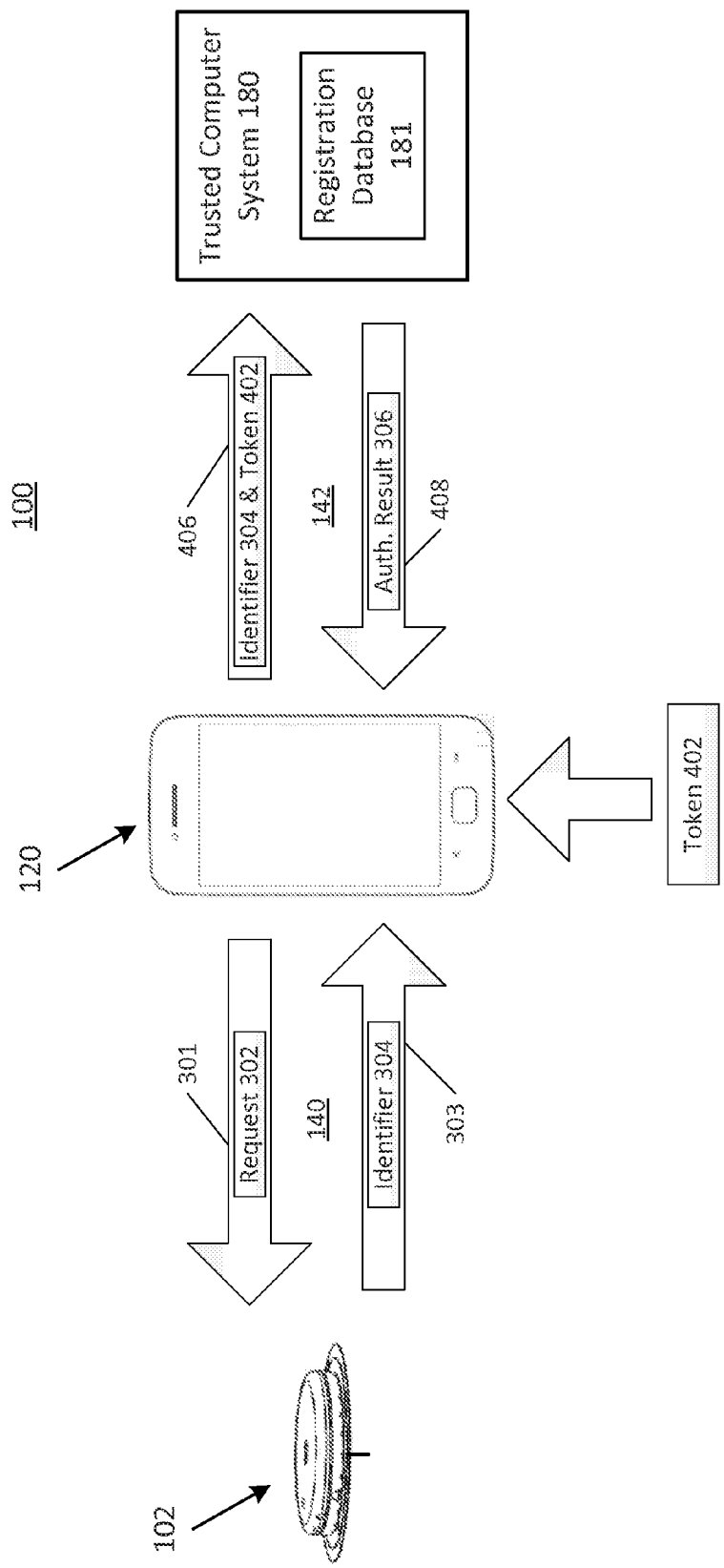

FIGS. 4 and 5A-B are illustrations depicting additional example embodiments of system 100 and the use thereof. In these embodiments, system 100 utilizes both an identifier 304 and a token 402. Token 402, in most embodiments, is a unique value associated with identifier 304 for a particular sensor control device 102 during the manufacturing process, and is stored together with identifier 304 within the memory of sensor control device 102. In many cases, one and only one token 402 is associated with each identifier 304. However, in some instances it may be desirable to associate multiple tokens 402 with a single identifier 304, or multiple identifiers 304 with a single token 402. Token 402 can be chosen as a non-sequential, random, or pseudo-random string of characters (alphanumeric or otherwise) to minimize the risk that a third party will be able to forecast or correctly guess future tokens 402.

Generally, for purposes of authentication, the identifier 304 and token 402 are obtained from a particular sensor control device 102 (or its packaging, etc.) and input into reader 120. This obtained identifier 304 can then be used as an index to look up and retrieve a corresponding token 402 from a registration database, and this retrieved token 402 is compared with the token 402 obtained from the particular sensor control device 102 to determine if they match. A match can be treated as authentication of the sensor control device 102, and a mismatch can be treated as indicative of a counterfeit, reused, recycled, refurbished, or otherwise unauthorized sensor control device 102.

These embodiments may find particular suitability in implementations where identifier 304 is a non-random (e.g., sequential) serial number of the sensor control device 102 that might be predictable to a third party. The use of an additional random, non-sequential string of characters in the form of token 402 makes it more difficult, if not impossible, for third parties to accurately predict the token and forge sensor control devices 102.

Token 402 can be provided to reader device 120 in a number of different ways. In the embodiment of FIG. 4, token 402 is provided directly to reader 120 by sensor control device 102. Like the embodiments described with respect to FIGS. 3A and 3D, reader device 120 can send an identifier request 302 to sensor control device 102 in communication 301. Sensor control device 102 can respond by retrieving both an identifier 304 and a token 402 from memory and communicating the identifier 304 and token 402 to reader device 120 in communication 404. Reader device 120 can then send identifier 304 and token 402 to trusted computer system 180 in communication 406.

Trusted computer system 180 can verify the received identifier 304 against registration database 181 in a manner similar to that already described. In addition, or in the alternative, trusted computer system 180 can use identifier 304 as an index to locate and retrieve a token 402 that was associated with that specific identifier 304 by the manufacturer, for example, during the manufacturing process. Token 402 can be stored within database 181 as a data element associated with identifier 304 within a particular data structure, or in separate memory located outside of database 181 (within trusted computer system 180 or elsewhere).

The token 402 that is retrieved from database 181 can then be compared to the token 402 provided by reader device 120. If the two tokens 402 match, a positive authentication result 306 is generated and transmitted to reader device 120 in communication 408. Reader device 120 can be programmed to commence or continue normal operation with sensor control device 120 if a positive authentication result 306 is received. If the two tokens 402 do not match, then it is possible that sensor control device 120 is a counterfeit device (or a reused, refurbished, or recycled device, etc.) and authorization is withheld. A negative authentication result 306 is generated and transmitted to reader device 120 (in communication 408) instructing it to cease or terminate normal operation with sensor control device 102. Reader device 120 can, optionally, instruct the user of the same.

FIGS. 5A-B depict an alternative embodiment where token 402 is not provided directly by sensor control device 102, but rather is obtained indirectly with the assistance of the user. In FIG. 5A, sensor control device 102 is depicted within packaging 501. Packaging 501 includes a code 502 such as printed barcode 502 with information corresponding to token 402. An optical scanner 505 (e.g., a camera) of reader device 120 can optically scan barcode 502 to retrieve token 402.

Packaging 501 can be a container for any part of system 100 that is supplied to the user, and is not limited to the container for the actual sensor control device 102, itself. Packaging 501 can be a container for sensor control device 102 alone, a container for multiple sensor control devices 102 (e.g., a multi-pack), a container for sensor control device 102 in combination with inserter 150 (FIG. 1), a container for inserter 150 alone, and can refer to inserts, labels, instructions, manuals, or the like that are contained within or otherwise shipped with system 100. Barcode 502 is shown here as a two-dimensional barcode. Barcode 502 can also be a one-dimensional barcode, three-dimensional barcode and can be of any format (QR code, data matrix, maxicode, aztec code, QR code, etc.). Printed indicia other than barcodes can be used as well.

Any number of additional techniques can be used to provide token 402 to reader device 120. For example, token 402 can be printed in human readable form on package 501, e.g., on a holographic label, such that the user can manually enter token 402 into reader device 120. In another example, token 402 is stored in an RFID (or NFC) label on packaging 501 and is read using an RFID (or NFC) scanner that is part of reader device 120. Many smart phones that can serve as reader devices 120 are equipped with RFID or NFC scanners that can read such labels. Other machine-readable formats can be used to obtain token 402 from packaging 501 as well. In all of the examples described herein, the provision of token 402 to reader device 120 can be done at a time of the user's choosing or in response to a prompt to do so by reader device 120.

Turning to FIG. 5B, system 100 can be configured such that reader device 120 sends a request 302 in communication 301 to sensor control device 102 for an identifier 304. Sensor control device 102 communicates identifier 304 to reader device 120 in communication 303. Token 402 is provided to reader device 120 with the assistance of the user, e.g., such as by scanning token 402 from packaging as depicted in FIG. 5A. This can occur prior to the sending of communication 301, concurrently with the sending of communications 301 or 303, or after the receipt of communication 303 by reader device 120. Regardless, after token 402 is provided to reader device 120, it is forward to trusted computer system 180 in communication 406 and the authentication process continues through completion as described with respect to FIG. 4.

In the embodiments of FIGS. 4 and 5A-B, registration database 181 within the remotely located trusted computer system 180 can be used to verify that tokens 402 and identifiers 304 are authentic. The embodiment described with respect to FIG. 4 can be modified such that the various tokens 402 and identifiers 304 are stored within a local registration database (e.g., database 129) of reader device 120 in a manner similar to that described with respect to the trusted computer system's registration database 181 (see, e.g., FIG. 3D).

In such a configuration, reader device 120 would perform those tasks described with respect to FIG. 4 as being performed by trusted computer system 180 (e.g., retrieval of identifier 304 from the database and comparison with the identifier 304 obtained from sensor control device 102 to determine if they match, using identifier 304 as an index to locate token 402 within the database, comparison of token 402 from the database with the token 402 obtained from sensor control device 102 to determine if they match, optionally generating an authentication result, etc.). There would no longer be a need to send communications 406 and 408, and the need for an internet connection 142 would be obviated for purposes of authenticating a particular sensor control device (although an internet connection may be desired for other reasons, such as providing updates as to used identifiers and tokens to trusted computer system 180, so that updates can be disseminated to other reader devices and instances of unauthorized usage can be monitored, etc.).

In yet another embodiment, token 402 can be provided to reader device 120 in a manner similar to that described with respect to FIGS. 4 and 5A-B, but reader device 120 does not forward token 402 to trusted computer system 180. Instead, reader device sends only identifier 304 to trusted computer system 180, which can then retrieve the corresponding version of token 402 stored within registration database and send that retrieved version back to reader device 120 (with or without authentication result 306). Reader device 120 can then determine whether token 402 provided by sensor control device 102 matches the token 402 received from trusted computer system 180 and conclude whether or not sensor control device 102 is authentic.

A number of additional embodiments will now be described that make use of authentication techniques having multiple keys, such as asymmetric (public key) cryptography and/or symmetric cryptography. These embodiments can be used alone or with any of the other embodiments, such as those using identifiers and/or tokens, described herein.

In public key cryptography, both a public key and a private key are typically used. The private key can be associated with sensor control device 102 and the public key can be associated with reader device 120. For example, one of any number of key generation algorithms, which are known in the art, can be used to generate a private key and a corresponding public key. Examples of key generation algorithms that can be used include, but are not limited to RSA algorithms such as those described in the Public-Key Cryptography Standards (PKCS). Any desired key length can be used, but keys with longer lengths will typically provide more security. For example, key lengths of 128 bits, 256 bits, 512 bits, 1024 bits, 2048 bits, and 5096 bits, as well as others, can be used.

Figure 6:
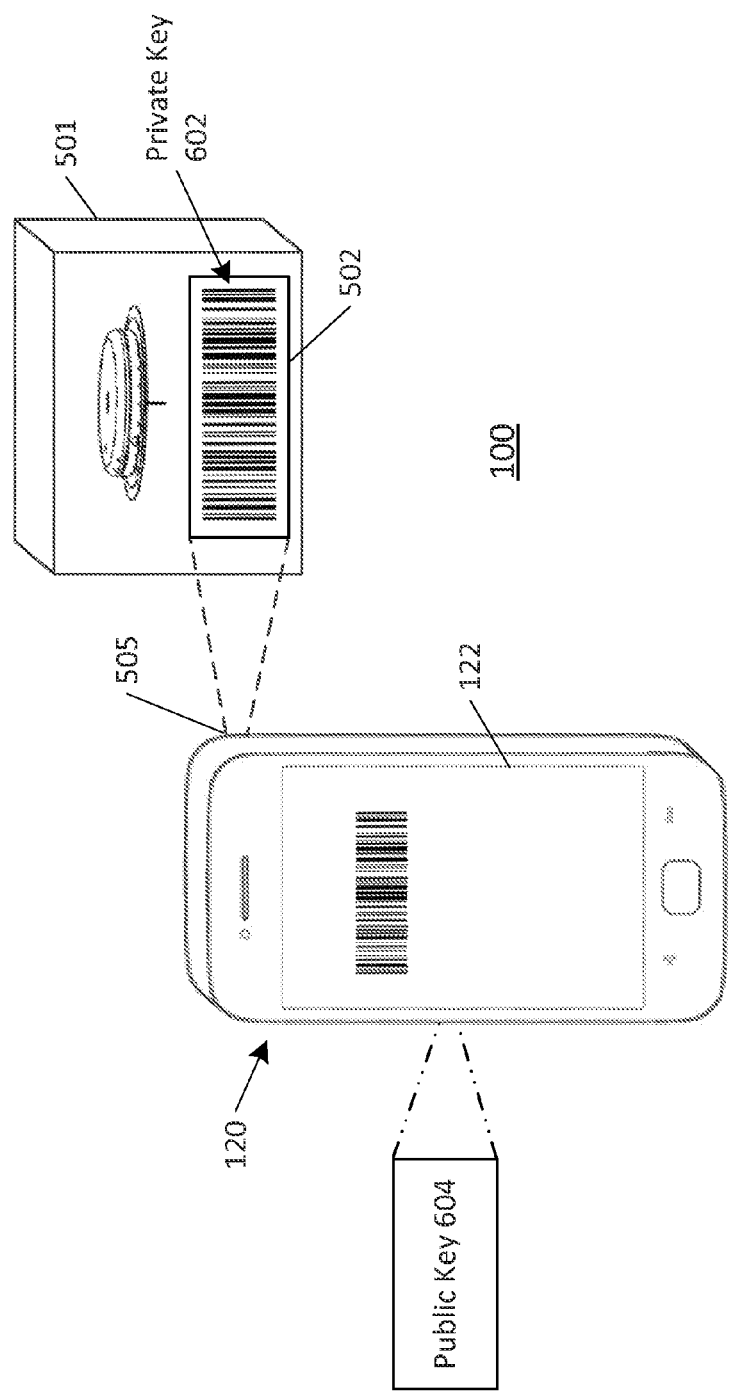

FIG. 6 depicts an example embodiment of system 100 utilizing both a private key 602 and a public key 604. Here, sensor control device packaging 501 has a barcode label 502 representing private key 602, which can be in an encrypted format. Optical scanner 505 of reader device 120 scans the barcode on label 502 and retrieves private key 602.

A public key 604 is stored within the memory of reader device 120. After reader device 120 obtains private key 602 and applies any required decryption algorithm to it, reader device 120 uses an algorithm stored thereon and public key 604 to algorithmically verify whether private key 602 is an authentic key, in accordance with techniques that will be readily apparent to those of ordinary skill in the art. If private key 602 is verified as authentic, then reader device 120 can initiate or continue normal operation with sensor control device 102. Conversely, if private key 602 is not verified as authentic, then it can be assumed that sensor control device 102 is counterfeit or otherwise not suitable for use, and reader device 120 ceases normal operation with sensor control device 102. While private key 602 is shown and described here as being optically represented on packaging 501 in barcode format, it should be noted that private key 602 can be associated with packaging 501 in any of the manners described with respect to the embodiments of FIGS. 5A-B. Also, private key 602 can be stored in the memory of sensor control device 102 during, for instance, manufacturing, and obtained by reader device 120 by communication over wired or wireless path 140.

In additional embodiments, private key 602 can be kept with the manufacturer, for example, with trusted computer system 180, and public key 604 can be stored in the memory of reader device 120 or sensor control device 102. In some embodiments, private key 602 can be used with a signing algorithm to generate a digital signature (or to digitally sign data) that is stored within non-volatile memory of sensor control device 102. Reader device 120 can be provided with this digital signature and can use public key 604 to algorithmically verify the authenticity of the signature. In these embodiments, trusted computer system 180 can act as a certificate authority (CA) or registration authority (RA) and can include a central directory as a repository for generated private keys, public keys, and/or digital signatures. The central directory can be a database that is separate from registration database 181, or it can be the same database.

Any desired technique or scheme that relies on public and private keys (e.g., key generation algorithms, signing algorithms, and signature verifying algorithms) can be used to implement the systems, devices, and methods described herein. These include, but are not limited to, techniques or schemes based on the RSA algorithms (and their variants), El Gamal algorithms (and their variants), Digital Signature Algorithm (DSA) (described in U.S. Pat. No. 5,231,668, which is incorporated by reference herein for all purposes) (and its variants), and elliptical curve-based algorithms (and its variants), and Rabin algorithms (and its variants).

In some embodiments, the digital signatures can be used with or within digital certificates (also referred to as public key certificates or identity certificates), for example, to bind a public key stored within a reader device to the individual that uses the reader device. The digital certificates can include any combination of the following (or information representative of the following): a serial number that uniquely identifies the digital signature, a subject (e.g., the user identified), the signing algorithm used to create signature, the digital signature itself, and identification of the issuer of the certificate, a date from which the certificate is first valid, a date to which the certificate is valid (e.g., an expiration date), a purpose of the public key, the public key itself, a thumbprint algorithm (the algorithm used to hash the certificate, if certificate is hashed), and the thumbprint (the hash itself, if used).

Figure 7:
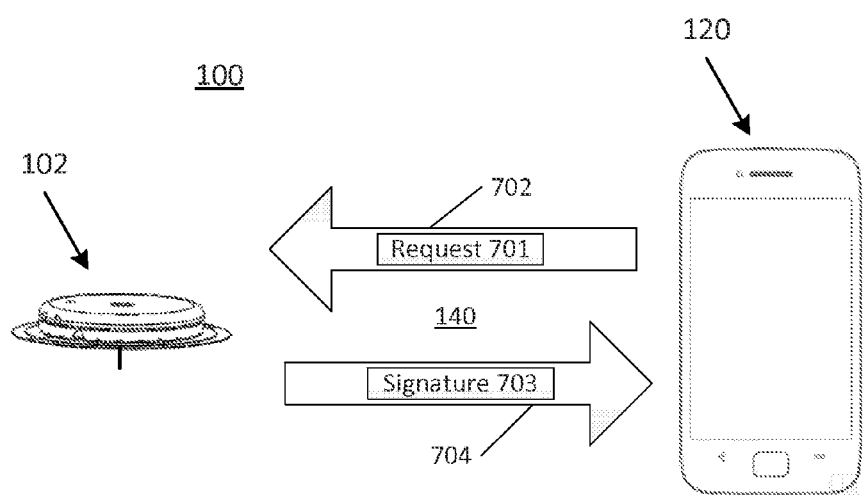

One such example embodiment using this approach is depicted in FIG. 7. Here, reader device 120 can optionally send a signature request 701 in communication 702 to sensor control device 102. In response, sensor control device 102 retrieves digital signature 703 from memory and communicates it to reader device 120 in communication 704. Reader device 120 can then perform a verification of signature 703 using public key 604, which is stored in the memory thereof. If the signature 703 is verified, reader device 120 can initiate or continue normal operation with sensor control device 102. Conversely, if signature 703 is determined to not be authentic, e.g., signature 703 fails the verification process, then reader device 120 can cease operation with sensor control device 102 and inform the user of the same.

In some embodiments, calibration parameters are determined for each sensor 104 during the manufacturing process and are stored in non-volatile memory of sensor control device 102. Some examples of these parameters are described in US Publication 2010/0230285, which is incorporated by reference herein for this and all other purposes. These calibration parameters can account for variations in the manufacturing process, and/or time-varying parameters (e.g., drift) of the sensor 104, and can be used to compensate for those variations and achieve accurate measurements of analyte levels. In some embodiments, digital signature 703 can be obtained by using a signing algorithm on private key 602 and the calibration parameters (e.g., the signed data) for that particular sensor control device 102. Digital signature 703 can be stored in the memory of sensor control device 102 along with a copy of those calibration parameters. Both digital signature 703 and the calibration parameters can be read from sensor control device 102 with reader device 120.

Reader device 120 can then apply a signature verifying algorithm to verify the authenticity of digital signature 703 and retrieve the calibration parameters from signature 703. The retrieved, unsigned calibration parameters can then be compared with those that were read directly from sensor control device 102 to see if they match. Because calibration parameters typically vary from sensor to sensor, a digital signature 703 that is copied from an authentic sensor control device 102 and reproduced on a counterfeit sensor control device 102 would contain calibration parameters that would almost certainly not match the actual calibration parameters stored within that sensor control device 102. Thus, counterfeiting would be deterred. Further, the calibration parameters can play a significant role in achieving accurate analyte measurements, and therefore a third-party would not be able to use copied calibration parameters without significantly compromising the accuracy of sensor control device 102. The matching of calibration parameters can be treated as verification of the particular sensor control device 102, and calibration parameters that differ can be treated as indicative of a counterfeit device 102.

Figure 8A:
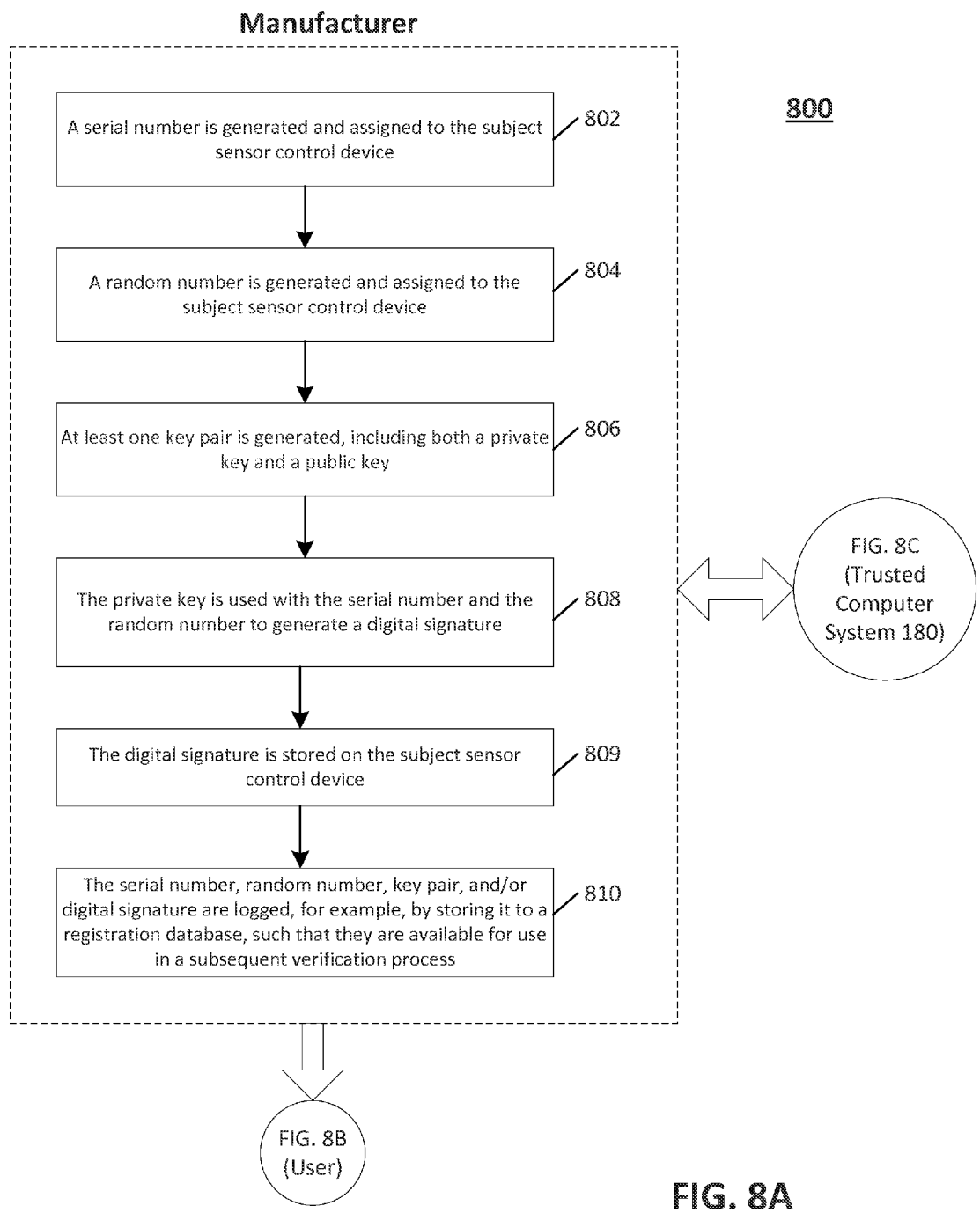
FIGS. 8A-C are flow diagrams depicting example embodiments of a method of operating an in vivo monitoring system having authentication capability.
Figure 8B:
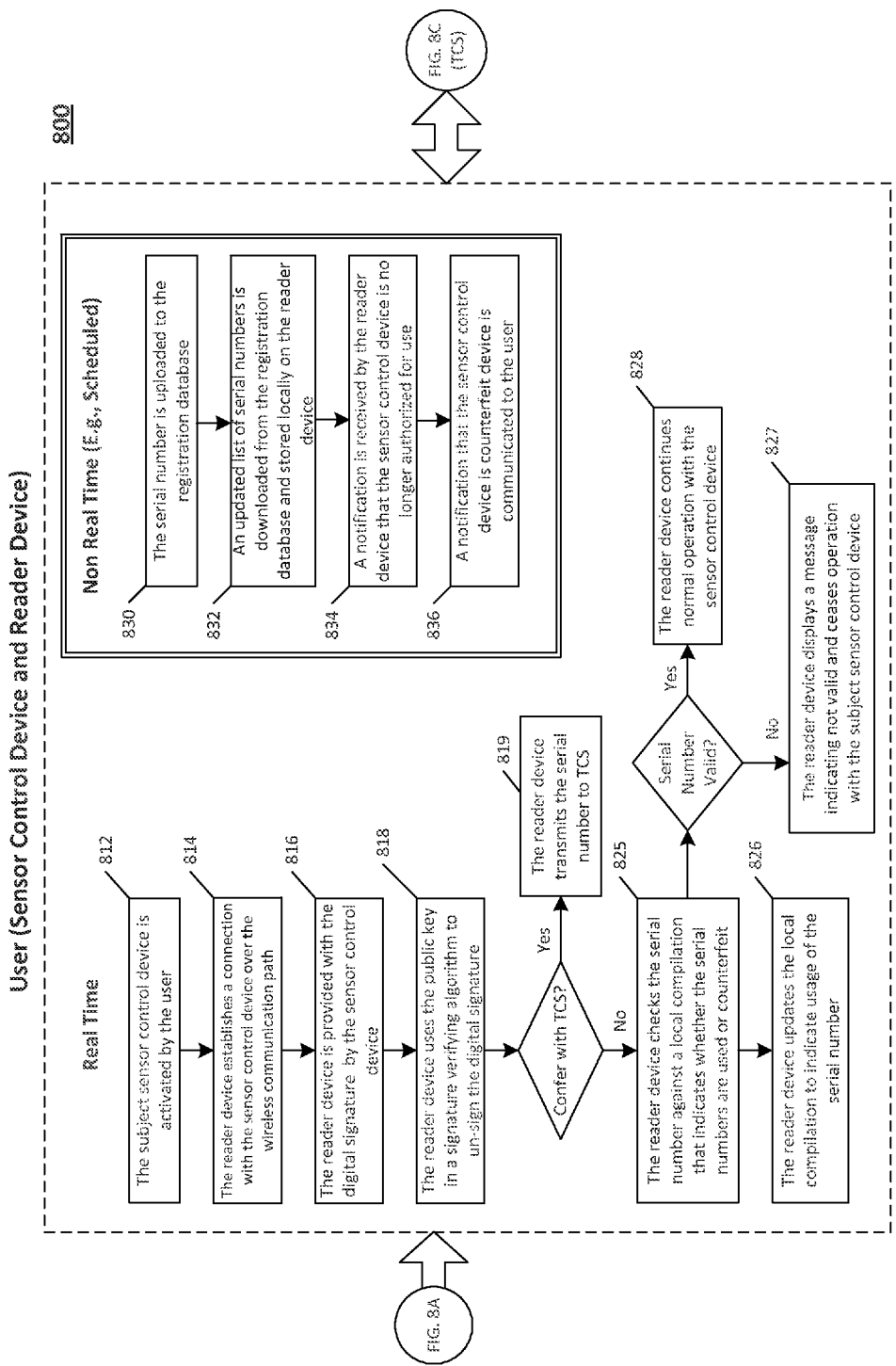
Figure 8C:
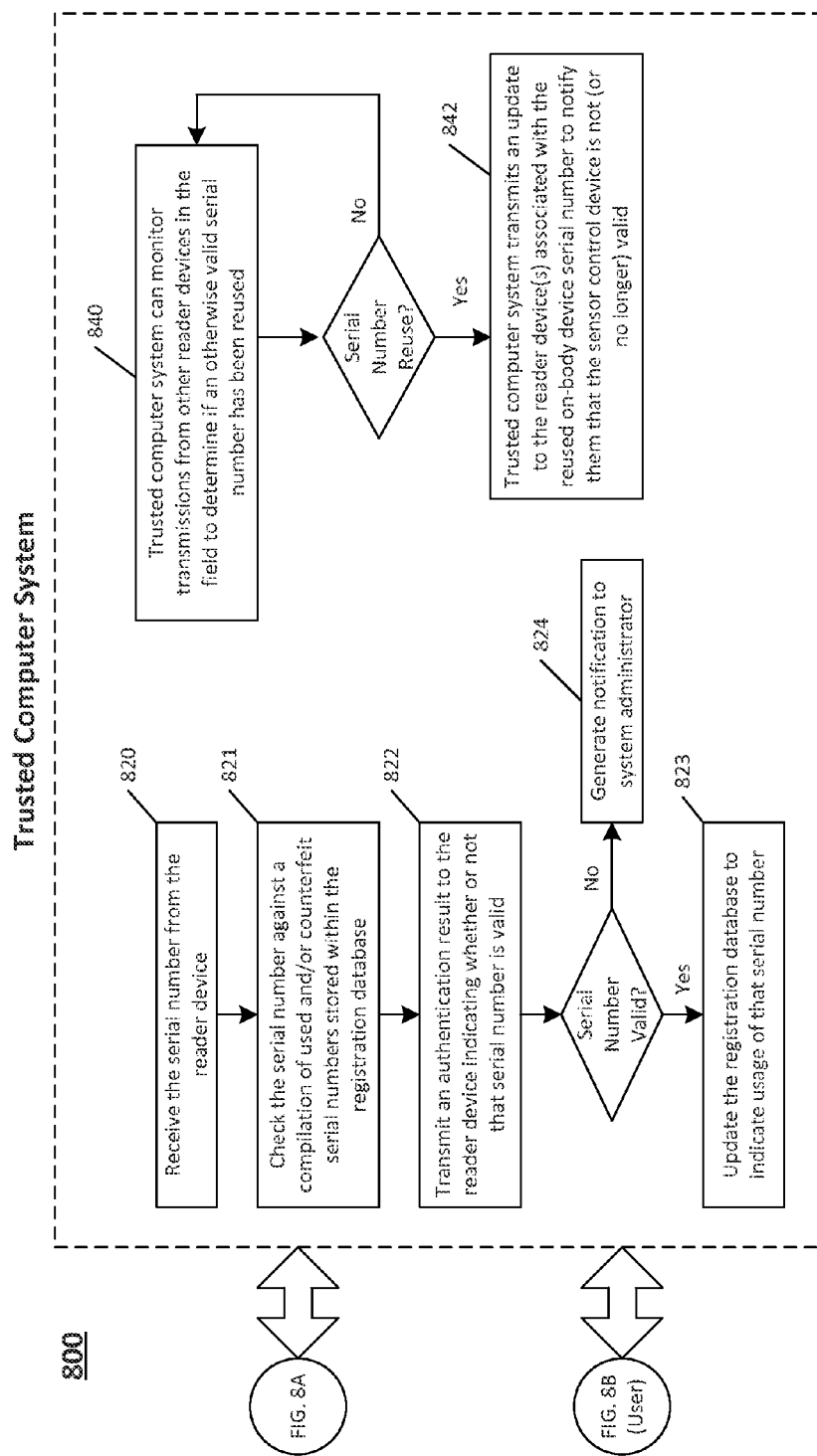

FIGS. 8A-C are flow diagrams depicting an example embodiment of a method 800 of using system 100. In this embodiment, each sensor control device 102 has an identifier 304 associated with it that includes a serial number and a random number, where the random number is used to increase the difficulty of predicting future values of authentic identifiers by a third party. Here, steps 802 through 810 can be performed by the manufacturer or distributor of system 100, or at least of sensor control device 102. In this example, both an identifier verification process and a key verification process are used, although it should be understood that either may be used by itself without the other.

It should be understood that, while FIGS. 8A-C are shown with steps occurring in a particular order, one of ordinary skill in the art will readily recognize that it is not necessary that the steps be performed in the specific order shown, and that variations in the order of performance of the steps, including performing steps simultaneously or with large periods of time in between, are within the scope of the present disclosure.

At 802, an identifier 304, which in this example is a serial number, is generated and assigned to the subject sensor control device 102. At 804, a random number is generated and assigned to the subject sensor control device 102. At 806, at least one key pair is generated, including both a private key 602 and a public key 604. In practice, a large number of keys may be generated during this step. At 808, private key 602 is used with the serial number and the random number to generate a digital signature 703, which is stored on the subject sensor control device 102 at 809. It should be noted that calibration parameters specific to sensor control device 102 can be used instead of, or in addition to the random number. Also, the serial number can be randomized to alleviate the need for a separate random number. At 810, the serial number, random number, key pair, and/or digital signature is logged, for example, by providing it to registration database 181 where it can be used later during the identifier verification process. Upon completing the manufacturing or configuration of sensor control device 102, it is directly or indirectly distributed to a user.

FIG. 8B depicts a compilation of steps or actions performed with sensor control device 102 and reader device 120, and thus would typically be performed by the user. Steps 812-828 are steps that can (but not necessarily) be performed in real-time, e.g., as the user is affirmatively interacting with sensor control device 102 and reader device 120 to set them up for operation, while steps 830-836 can be performed on a non-real-time basis, e.g., at a scheduled time when the user is not otherwise interacting with the system. At 812, the subject sensor control device 102 is activated by the user. This may occur in a number of ways, e.g., by pressing a switch, by unsealing device 102 from its packaging, by applying device 102 to the body, etc. At 814, reader device 120 establishes a connection with sensor control device 102 over communication path 140 (see, e.g., FIG. 1). While (or after) establishing the connection, at 816, reader device 120 is provided with digital signature 703 by sensor control device 102. Then, at 818, reader device 120 uses public key 604, which was previously stored in the memory of reader device 120, or was previously retrieved from the manufacturer (e.g., over the internet from trusted computer system 180), in a signature verifying algorithm to reduce digital signature 703 and obtain the serial number and random number contained therein.

If it is desired to confer with trusted computer system 180 for authentication purposes (e.g., an internet connection is available), then at 819 reader device 120 can transmit the serial number to trusted computer system 180, which can receive it at 820. Step 820 is depicted in FIG. 8C, which illustrates the steps that can be performed at or with trusted computer system 180. Referring still to FIG. 8C, at 821, trusted computer system 180 checks the serial number against a compilation of used serial numbers and a compilation of counterfeit serial numbers (which may be the same compilation) that is stored within registration database 181 to see if that serial number has been used already or is known (or suspected) to be counterfeit.

At 822, trusted computer system 180 will transmit an authentication result to reader device 120 indicating whether or not that serial number is valid, e.g., suitable for use or not counterfeit. If the serial number is valid, then at 823, trusted computer system 180 can update registration database 181 to indicate usage of that serial number. If the serial number is not valid, then at 824 a system notification or alarm can be generated to notify the administrator of trusted computer system 180 that a potential counterfeiting has occurred, so that the incident can be investigated accordingly. At 840, which may be a continuous act, trusted computer system 180 can monitor transmissions from other reader devices 120 in the field to determine if the valid serial number is received from another source. If it is received, then that can be indicative of counterfeiting. At 842, trusted computer system 180 can transmit, or broadcast, an update to the reader devices 120 associated with the counterfeit sensor control device 102 to notify them that such device is not (or no longer) valid.

Referring back to FIG. 8B, if it is desired not to confer with trusted computer system 180, e.g., no internet connection is available or if it is desired to avoid performing an internet transaction (such as to save time), etc., then at 825 reader device 120 can check the serial number against a local compilation of serial numbers that indicates whether the serial numbers are used or counterfeit (e.g., database 129). If the serial number is not already used, or not suspected to be counterfeit, then, at 826, reader device 120 can update the local compilation to indicate usage of that serial number.

If it is determined that the serial number is not valid, either through receipt of the authentication result from trusted computer system 180 or through a local determination at reader device 120, then, at 827 reader device 120 displays a message to the user indicating the same and ceases operation with the subject sensor control device 120. If it is determined that the serial number is valid, then, at 828 reader device 120 continues with normal operation with sensor control device 102, including the collection and display of sensed analyte data from sensor control device 102.

When an internet connection again becomes available, or at a scheduled or convenient time, at 830, the serial number can be uploaded to registration database 181 so that it can be added to the compilation of used serial numbers stored therein. Also, at 832, an updated list of used serial numbers and/or suspected counterfeit serial numbers can be downloaded from registration database 181 and stored locally on reader device 120. If it is later determined or suspected that the serial number of sensor control device 102 is a counterfeit, then trusted computer system 180 can send a notification or alarm to reader device 120 indicating that the sensor control device is no longer authorized for use (e.g., 842 in FIG. 8C), which can be received by reader device 120 at 834 (FIG. 8B). At 836, a notification that a counterfeit device is being used is displayed or otherwise communicated to the user. An acknowledgment by the user that this notification has been read and understood may be required prior to terminating operation with the counterfeit sensor control device 102.

It should be understood that, for all of the example embodiments described herein where communications are sent from reader device 120 to trusted computer system 180 over the internet for the purposes of authentication, those embodiments can be modified such that the authentication information stored at trusted computer system 180 (e.g., information stored within registration database 181) is instead stored within reader device 120, and reader device 120 can perform the authentication processes itself. In these cases, reader device 120 can later verify its determination as to the authenticity of sensor control device 102 by communication with trusted computer system 180, either by having trusted computer system 180 conduct its own verification, or by downloading relatively more current authentication information from trusted computer system 180 and re-verifying the authenticity of sensor control device 102. Likewise, for all of the example embodiments described herein where reader device 120 performs its own authentication of sensor control device 102 without communication over the internet (e.g., by reference to a locally stored registration database), these embodiments can be modified such that reader device 120 instead relies upon trusted computer system 180 to perform the authentication of sensor control device 102 by communicating the requisite authentication information to trusted computer system 180 over the internet and by receiving an authentication result from trusted computer system 180.

For each embodiment disclosed herein, software and other mechanisms can be provided for logging and monitoring instances where the authentication process results in a sensor control device not being authenticated, in order to identify similarities and/or patterns that can be indicative of localized, widespread, or systematic abuse. For example, repeated use of the same identifier in a particular region can be indicative of counterfeiting within that region, in which case the manufacturer can take corrective steps. The logging and/or monitoring function can be performed by trusted computer system 180 (or an administrator thereof), reader device 120, or another device or system. In addition to the region of sale or use, instances of unauthorized usage can be correlated to the identifier, token, private or public key, identity of the user, identity of the distributor, identity of the hospital or medical professional, model number of the sensor control device or reader device, serial number of the sensor control device or reader device, network address (e.g., IP address) of the reader device, insurer, insurance account, any combination of two or more of the aforementioned types of information, and the like.

Sensor Configurations

Analytes that may be monitored with system 100 include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

Analyte sensor 104 may include an analyte-responsive enzyme to provide a sensing element. Some analytes, such as oxygen, can be directly electrooxidized or electroreduced on sensor 104, and more specifically at least on a working electrode (not shown) of a sensor 104. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

A variety of different sensing element configurations may be used. In certain embodiments, the sensing elements are deposited on the conductive material of a working electrode. The sensing elements may extend beyond the conductive material of the working electrode. In some cases, the sensing elements may also extend over other electrodes, e.g., over the counter electrode and/or reference electrode (or counter/reference where provided). In other embodiments, the sensing elements are contained on the working electrode, such that the sensing elements do not extend beyond the conductive material of the working electrode. In some embodiments a working electrode is configured to include a plurality of spatially distinct sensing elements. Additional information related to the use of spatially distinct sensing elements can be found in US Provisional Application No. 61/421,371, entitled "Analyte Sensors with Reduced Sensitivity Variation," which was filed on Dec. 9, 2010, and which is incorporated by reference herein in its entirety and for all purposes.

The terms "working electrode", "counter electrode", "reference electrode" and "counter/reference electrode" are used herein to refer to conductive sensor components, including, e.g., conductive traces, which are configured to function as a working electrode, counter electrode, reference electrode or a counter/reference electrode respectively. For example, a working electrode includes that portion of a conductive material, e.g., a conductive trace, which functions as a working electrode as described herein, e.g., that portion of a conductive material which is exposed to an environment containing the analyte or anlaytes to be measured, and which, in some cases, has been modified with one or more sensing elements as described herein. Similarly, a reference electrode includes that portion of a conductive material, e.g., conductive trace, which function as a reference electrode as described herein, e.g., that portion of a conductive material which is exposed to an environment containing the analyte or anlaytes to be measured, and which, in some cases, includes a secondary conductive layer, e.g., a Ag/AgCl layer. A counter electrode includes that portion of a conductive material, e.g., conductive trace which is configured to function as a counter electrode as described herein, e.g., that portion of a conductive trace which is exposed to an environment containing the analyte or anlaytes to be measured. As noted above, in some embodiments, a portion of a conductive material, e.g., conductive trace, may function as either or both of a counter electrode and a reference electrode. In addition, "working electrodes", "counter electrodes", "reference electrodes" and "counter/reference electrodes" may include portions, e.g., conductive traces, electrical contacts, or areas or portions thereof, which do not include sensing elements but which are used to electrically connect the electrodes to other electrical components.

Sensing elements that are in direct contact with the working electrode, e.g., the working electrode trace, may contain an electron transfer agent to transfer electrons directly or indirectly between the analyte and the working electrode, and/or a catalyst to facilitate a reaction of the analyte. For example, a glucose, lactate, or oxygen electrode may be formed having sensing elements which contain a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments the sensing elements are not deposited directly on the working electrode, e.g., the working electrode trace. Instead, the sensing elements may be spaced apart from the working electrode trace, and separated from the working electrode trace, e.g., by a separation layer. A separation layer may include one or more membranes or films or a physical distance. In addition to separating the working electrode trace from the sensing elements, the separation layer may also act as a mass transport limiting layer and/or an interferent eliminating layer and/or a biocompatible layer.

In certain embodiments which include more than one working electrode, one or more of the working electrodes may not have corresponding sensing elements, or may have sensing elements that do not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing elements by, for example, subtracting the signal.

In certain embodiments, the sensing elements include one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly (vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation.

Another example of an ionically-bound mediator is a positively charged polymer including quaternized poly (4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. These sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc. A mass transport limiting layer may be applied to an analyte sensor as described herein via any of a variety of suitable methods, including, e.g., dip coating and slot die coating.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly (ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over the enzyme-containing sensing elements and allowing the solution to cure for about one to two days or other appropriate time period. The crosslinker-polymer solution may be applied over the sensing elements by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. In order to coat the distal and side edges of the sensor, the membrane material may have to be applied subsequent to singulation of the sensor precursors. In some embodiments, the analyte sensor is dip-coated following singulation to apply one or more membranes. Alternatively, the analyte sensor could be slot-die coated wherein each side of the analyte sensor is coated separately. A membrane applied in the above manner may have any combination of the following functions: (1) mass transport limitation, i.e., reduction of the flux of analyte that can reach the sensing elements, (2) biocompatibility enhancement, or (3) interferent reduction.

In some embodiments, a membrane composition for use as a mass transport limiting layer may include one or more leveling agents, e.g., polydimethylsiloxane (PDMS). Additional information with respect to the use of leveling agents can be found, for example, in US Patent Application Publication No. US 2010/0081905, the disclosure of which is incorporated by reference herein in its entirety.

In some instances, the membrane may form one or more bonds with the sensing elements. The term "bonds" is intended to cover any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing elements. In certain embodiments, crosslinking of the membrane to the sensing element facilitates a reduction in the occurrence of delamination of the membrane from the sensor.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of authentication in an in vivo analyte monitoring system, comprising:
   receiving, by a reader device, an identifier from a sensor control device over a local wireless communication path, wherein the sensor control device comprises a sensor and analyte monitoring circuitry, and wherein the sensor is adapted to be inserted into a body of a user;
   verifying, at the reader device, that the identifier is in the proper format or does not belong to a class of sensor control devices that are not for operation with the reader device;
   sending the identifier from the reader device over an internet to a trusted computer system having a stored registration database; and
   receiving, by the reader device, an authentication result from the trusted computer system over the internet, wherein the authentication result indicates whether the sensor control device is or is not authorized to operate with the reader device.

2. The method of claim 1, further comprising sending an identification request from the reader device over the local wireless communication path to the sensor control device, wherein the sensor control device sends the identifier to the reader device in response to receipt of the identification request.

3. The method of claim 1, further comprising determining, by the trusted computer system, authenticity of the identifier by reference to a stored registration database.

4. The method of claim 3, wherein, if the identifier is in the stored registration database, determining if the identifier is associated with an unused device.

5. The method of claim 3, wherein the registration database comprises one or more compilations of used and unused identifiers.

6. The method of claim 3, further comprising updating the registration database by associating the identifier with a used device.

7. The method of claim 1, wherein the authentication result authorizes the reader device to operate with the sensor control device if the identifier is associated with an unused device, and wherein the authentication result does not authorize the reader device to operate with the sensor control device if the identifier is associated with a device that has already been used or is counterfeit.

8. The method of claim 7, wherein, if the authentication result does not authorize the reader device to operate with the sensor control device, the method further comprises ceasing communication, by the reader device, with the sensor control device.

9. The method of claim 7, wherein, if the authentication result does not authorize the reader device to operate with the sensor control device, the method further comprises displaying a message on a display of the reader device indicating that the sensor control device is not authorized for use.

10. The method of claim 1, wherein the reader device communicates with the sensor control device over the local wireless communication path using a near field communication (NFC) protocol.

11. The method of claim 1, wherein the reader device communicates with the sensor control device over the local wireless communication path using a radio frequency identification (RFID) protocol.

12. The method of claim 1, wherein the reader device communicates with the sensor control device over the local wireless communication path using either a Bluetooth or Bluetooth Low Energy protocol.

13. The method of claim 1, wherein the identifier is a sensor identification (ID) number stored in a memory of the sensor.

14. The method of claim 1, wherein the reader device is a smart phone.

15. The method of claim 1, wherein the reader device comprises location determining hardware capable of determining a current location of the reader device, and the method further comprises sending the identifier and the current location of the reader device over the internet to the trusted computer system.

16. The method of claim 15, wherein the authentication result authorizes the reader device to operate with the sensor control device if the identifier is indicative of an unused device and the identifier is authorized for use in the current location, and wherein the authentication result does not authorize the reader device to operate with the sensor control device if the identifier is indicative of a device that has already been used or the identifier is not authorized for use in the current location.

17. The method of claim 16, further comprising, if the identifier is not authorized for use in the current location, displaying a message on a display of the reader device indicating that the sensor control device is not authorized for use in the current location.

18. The method of claim 1, further comprising, if the authentication result permits operation of the reader device with the sensor control device and if the sensor has been inserted into the body of the user, then:
  reading, with the reader device, information indicative of an analyte level of the user from the sensor control device; and
  displaying the analyte level on a display of the reader device.

19. The method of claim 1, further comprising:
  receiving, at the reader device, at least one calibration parameter from the sensor control device, and
  comparing, at the reader device, the received at least one calibration parameter with at least one digitally signed calibration parameter stored on the reader device.

20. The method of claim 1, wherein the authentication result is generated at the trusted computer system.

* * * * *